(12) United States Patent
Yoon et al.

(10) Patent No.: US 12,114,664 B2
(45) Date of Patent: Oct. 15, 2024

(54) SALMONELLA TYPHIMURIUM BACTERIOPHAGE STP-2 AND USE THEREOF FOR INHIBITING PROLIFERATION OF SALMONELLA TYPHIMURIUM

(71) Applicant: Intron Biotechnology, Inc., Gyeonggi-do (KR)

(72) Inventors: Seong Jun Yoon, Seoul (KR); Soo Youn Jun, Seoul (KR); Jee Soo Son, Seoul (KR); Hyoun Rok Paik, Incheon (KR); Beom Seok Kim, Seoul (KR); Sang Hyeon Kang, Seoul (KR)

(73) Assignee: INTRON BIOTECHNOLOGY, INC., Gyeonggi-Do (CN)

( * ) Notice: Subject to any disclaimer, the term of this patent is extended or adjusted under 35 U.S.C. 154(b) by 1034 days.

(21) Appl. No.: 17/043,847

(22) PCT Filed: Feb. 19, 2019

(86) PCT No.: PCT/KR2019/001942
§ 371 (c)(1),
(2) Date: Sep. 30, 2020

(87) PCT Pub. No.: WO2019/198925
PCT Pub. Date: Oct. 17, 2019

(65) Prior Publication Data
US 2021/0054345 A1     Feb. 25, 2021

(30) Foreign Application Priority Data
Apr. 11, 2018 (KR) .................. 10-2018-0041975

(51) Int. Cl.
| | | |
|---|---|---|
| C12N 7/00 | (2006.01) |
| A01N 63/40 | (2020.01) |
| A23K 10/16 | (2016.01) |
| A23L 2/52 | (2006.01) |
| A23L 33/10 | (2016.01) |
| A61K 35/76 | (2015.01) |
| A61P 31/04 | (2006.01) |

(52) U.S. Cl.
CPC .............. *A01N 63/40* (2020.01); *A23K 10/16* (2016.05); *A23L 2/52* (2013.01); *A23L 33/10* (2016.08); *A61K 35/76* (2013.01); *A61P 31/04* (2018.01); *C12N 7/00* (2013.01); *A23V 2002/00* (2013.01); *C12N 2795/10321* (2013.01); *C12N 2795/10331* (2013.01); *C12N 2795/10332* (2013.01)

(58) Field of Classification Search
None
See application file for complete search history.

(56) References Cited

FOREIGN PATENT DOCUMENTS

| | | |
|---|---|---|
| EP | 3 133 153 A1 | 2/2017 |
| KR | 10-2009-0030532 | 3/2009 |
| KR | 10-2013-0021677 | 3/2013 |
| KR | 10-2013-0031004 | 3/2013 |
| KR | 10-2015-0118835 | 10/2015 |
| WO | WO 2013/042964 | 3/2013 |
| WO | WO 2019/198925 | 10/2019 |

OTHER PUBLICATIONS

Choi et al. (Applied and Environmental Microbiology, 2013, vol. 79, p. 4829-4837).*
PCT, PCT/KR2019/001942 (WO2019/198925), Feb. 19, 2019, (Oct. 17, 2019), Intron Biotechnology, Inc.
International Search Report and Written Opinion were mailed on Jun. 10, 2019 by the International Searching Authority for International Application No. PCT/KR2019/001942, filed on Feb. 19, 2019 and published as WO 2019/198925 on Oct. 17, 2019 (Applicant—Intron Biotechnology, Inc.) (10 Pages).
Choi, Y. et al., "Identification and Characterization of a Novel Flagellum-Dependent *Salmonella*-Infecting Baceteriphage," iEPS5, Applied and Environmental Microbiology (2013), vol. 79, No. 16, pp. 4829-4837.
Pereira, C. et al., "Bacteriophages with Potential to Inactivate Salmonella Typhimurium: Use of Single Phage Suspensions and Phage Cocktails," Virus Research (2016), vol. 220, pp. 179-192.

* cited by examiner

*Primary Examiner* — Agnieszka Boesen
(74) *Attorney, Agent, or Firm* — BALLARD SPAHR LLP

(57) ABSTRACT

The present invention relates to a *Siphoviridae* bacteriophage STP-2 (Accession number: KCTC 12853BP) isolated from nature and characterized by having the ability to destroy *Salmonella Typhimurium* and having a genome represented by SEQ ID NO:1; and to a method for preventing and treating diseases caused by *Salmonella Typhimurium* using *Siphoviridae* bacteriophage STP-2 containing the same as an active ingredient.

2 Claims, 3 Drawing Sheets
Specification includes a Sequence Listing.

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM
RECEIPT FOR ORIGINAL DEPOSIT
issued pursuant to Rule 7.1

NAME OF DEPOSITOR: iNtRON Biotechnology, INC.
ADDRESS: 903, Joongang Induspia 5$^{th}$, 137 Sagimakgol-ro, Jungwon-gu, Seongnam-si, Gyeonggi-do, Republic of Korea (Postal code, 13202)

I. IDENTIFICATION OF THE MICROORGANISM

| Identification reference given by the DEPOSITOR: | Accession number given by the INTERNATIONAL DEPOSITARY AUTHORITY: |
|---|---|
| Bacteriophage STP-2 | KCTC 12853BP |

II. SCIENTIFIC DESCRIPTION AND PROPOSED TAXONOMIC DESIGNATION

The microorganism identified under I above was accompanied by:
[x] a scientific description
[ ] a proposed taxonomic designation

III. RECEIPT AND ACCEPTANCE

This International Depositary Authority accepts the microorganism identified under I above, which was received thereby on June 23, 2015.

V. INTERNATIONAL DEPOSITARY AUTHORITY

| Name: Korean Collection for Type Cultures | Signature(s) of person(s) having power to represent the International Depositary Authority or of authorized official(s): |
|---|---|
| Address: Biological Resource Center in Korea Research Institute of Bioscience & Biotechnology (KRIBB), 125 Gwahak-ro, Yuseong-gu, Daejeon, Republic of Korea (305-806) | Representative<br><br>July 02, 2015 |

FIG. 3

SALMONELLA TYPHIMURIUM BACTERIOPHAGE STP-2 AND USE THEREOF FOR INHIBITING PROLIFERATION OF SALMONELLA TYPHIMURIUM

CROSS-REFERENCE TO RELATED APPLICATIONS

This application is a U.S. National Phase Application of International Application No. PCT/KR2019/001942, filed Feb. 19, 2019, which claims priority to Korean Application No. 10-2018-0041975, filed Apr. 11, 2018, each of which are hereby incorporated by reference in their entirety.

REFERENCE TO SEQUENCE LISTING

The Sequence Listing submitted concurrently with this preliminary amendment as a text file named "08162_0066U1_Sequence_Listing.txt," created on Sep. 30, 2020, and having a size of 75,278 bytes is hereby incorporated by reference pursuant to 37 C.F.R. § 1.52(e)(5).

TECHNICAL FIELD

The present invention relates to a bacteriophage isolated from nature, which infects *Salmonella Typhimurium* to thus kill *Salmonella Typhimurium*, and a method of preventing and treating diseases caused by *Salmonella Typhimurium* using a composition containing the same as an active ingredient. More particularly, the present invention relates to a *Siphoviridae* bacteriophage STP-2 (Accession number: KCTC 12853BP) isolated from nature, which has the ability to kill *Salmonella Typhimurium* and has the genome represented by SEQ ID NO: 1, and a method of preventing or treating diseases caused by *Salmonella Typhimurium* using a composition containing the above bacteriophage as an active ingredient.

BACKGROUND ART

*Salmonella* is a gram-negative *bacillus* belonging to the Enterobacteriaceae family, and is taxonomically divided into two species, namely *Salmonella enterica* and *Salmonella bongori*, and is further subdivided into 5 groups and 6 subspecies. Depending on individual groups and subspecies, *Salmonella* bacteria belonging to Group I are *S. enterica* subsp. *enterica* and *Salmonella* belonging to Group II are *S. enterica* subsp. *salamae*. Group III is subdivided into IIIa and IIIb, and *Salmonella* bacteria belonging to IIIa and IIIb are *S. enterica* subsp. *arizonae* and *S. enterica* subsp. *diarizonae*, respectively. Moreover, *Salmonella* bacteria belonging to Group IV and Group V are *S. enterica* subsp. *houtenae* and *S. enterica* subsp. *bongori*, respectively. In addition, *Salmonella* bacteria are classified into various serotypes based on a combination of bacterial antigens and flagella antigens, in addition to biochemical classification, and 58 types of bacterial antigens and 114 types of flagella antigens have been identified to date, and it is known that there is a total of 2,659 serotypes based on the combination of individual antigens. *Salmonella* bacteria have a wide range of hosts, from mammals including humans to birds and reptiles, and are generally known as pathogens that infect humans, livestock, pets and wild animals. The main serotypes of *Salmonella* that cause food poisoning are *Salmonella Typhimurium*, *Salmonella Enteritidis* and the like. Since 1984, the incidence of food poisoning attributable to *Salmonella* began to increase in Europe and the United States, and since 1988, the number of cases of food poisoning caused by *Salmonella* has drastically increased around the world, greatly increasing interest in *Salmonella*.

Meanwhile, *Salmonella Typhimurium* may cause digestive diseases in livestock such as pigs, etc. Although various antibiotics have been used for the prevention or treatment of diseases caused by *Salmonella Typhimurium*, the incidence of bacteria resistant to such antibiotics is increasing these days, and thus the development of measures other than antibiotics is urgent. In particular, the advent of multidrug-resistant *Salmonella Typhimurium* DT104 has become a social problem due to concerns about transmission to humans through livestock products and the lack of appropriate therapeutic agents.

Recently, the use of bacteriophages as a countermeasure against infectious bacterial diseases has attracted considerable attention. In particular, these bacteriophages are receiving great attention due to strong antibacterial activity against antibiotic-resistant bacteria. Bacteriophages are very small microorganisms infecting bacteria, and are usually simply called "phages". Once a bacteriophage infects a bacterium, the bacteriophage proliferates inside the bacterial cell. After proliferation, the progeny of the bacteriophage destroy the bacterial cell wall and escape from the host bacteria, demonstrating that the bacteriophage has the ability to kill bacteria. The manner in which the bacteriophage infects bacteria is characterized by the very high specificity thereof, and thus the range of types of bacteriophages that infect a specific bacterium is limited. That is, a certain bacteriophage may infect only a specific bacterium, suggesting that a certain bacteriophage is capable of providing an antibacterial effect only for a specific bacterium. Due to this bacterial specificity of bacteriophages, the bacteriophage confers antibacterial effects only upon a target bacterium, but does not affect commensal bacteria in the environment or in the intestines of animals. Conventional antibiotics, which have been widely used for bacterial treatment, incidentally influence many other kinds of bacteria. This causes problems such as environmental pollution and the disturbance of normal microflora in animals. In contrast, the use of bacteriophages does not disturb normal microflora in animals, because the target bacterium is selectively killed. Hence, bacteriophages may be utilized safely, which thus greatly lessens the probability of adverse effects of use thereof compared to antibiotics.

Bacteriophages were first discovered by the English bacteriologist Twort in 1915 when he noticed that *Micrococcus* colonies softened and became transparent due to something unknown. In 1917, the French bacteriologist d'Herelle discovered that *Shigella dysenteriae* in a filtrate of dysentery patient feces was destroyed by something, and further studied this phenomenon. As a result, he independently identified bacteriophages, and named them bacteriophages, which means "eater of bacteria". Since then, bacteriophages acting against such pathogenic bacteria as *Shigella, Salmonella Typhi*, and *Vibrio cholerae* have been continually identified.

Owing to the unique ability of bacteriophages to kill bacteria, bacteriophages have attracted attention as a potentially effective countermeasure against bacterial infection since their discovery, and a lot of research related thereto has been conducted. However, since penicillin was discovered by Fleming, studies on bacteriophages have continued only in some Eastern European countries and the former Soviet Union, because the spread of antibiotics was generalized. Since 2000, the limitations of conventional antibiotics have become apparent due to the increase in antibiotic-resistant bacteria, and the possibility of developing bacteriophages as a substitute for conventional antibiotics has been highlighted, and thus bacteriophages are again attracting attention as antibacterial agents.

As described above, bacteriophages tend to be highly specific for target bacteria. Because of the high specificity of bacteriophages to bacteria, bacteriophages frequently exhibit an antibacterial effect only for certain strains of bacteria, even within the same species. In addition, the antibacterial strength of bacteriophages may vary depending on the target bacterial strain. Therefore, it is necessary to collect many kinds of bacteriophages that are useful in order to effectively control specific bacteria. Hence, in order to develop an effective bacteriophage utilization method for controlling *Salmonella Typhimurium*, many kinds of bacteriophages that exhibit antibacterial effects against *Salmonella Typhimurium* must be acquired. Furthermore, the resulting bacteriophages need to be screened as to whether or not they are superior to others from the aspects of antibacterial strength and spectrum.

DISCLOSURE

Technical Problem

Therefore, the present inventors endeavored to develop a composition applicable for the prevention and treatment of diseases caused by *Salmonella Typhimurium* using a bacteriophage that is isolated from nature and is capable of killing *Salmonella Typhimurium*, and further to establish a method of preventing and treating diseases caused by *Salmonella Typhimurium* using the composition. As a result, the present inventors isolated a bacteriophage suitable for this purpose from nature and determined the sequence of the genome, which distinguishes the isolated bacteriophage from other bacteriophages. Then, the present inventors developed a composition containing the bacteriophage as an active ingredient and ascertained that this composition is capable of being effectively used to prevent and treat diseases caused by *Salmonella Typhimurium*, thus culminating in the present invention.

Accordingly, an objective of the present invention is to provide a *Siphoviridae* bacteriophage STP-2 (Accession number: KCTC 12853BP) isolated from nature, which has the ability to specifically kill *Salmonella Typhimurium* and has the genome represented by SEQ ID NO: 1.

Another objective of the present invention is to provide a composition applicable for preventing or treating diseases caused by *Salmonella Typhimurium*, which contains, as an active ingredient, an isolated bacteriophage STP-2 (Accession number: KCTC 12853BP), infecting *Salmonella Typhimurium*, to thus kill *Salmonella Typhimurium*.

Still another objective of the present invention is to provide a method of preventing and treating diseases caused by *Salmonella Typhimurium* using the composition applicable for preventing and treating diseases caused by *Salmonella Typhimurium*, which contains, as an active ingredient, the isolated bacteriophage STP-2 (Accession number: KCTC 12853BP), infecting *Salmonella Typhimurium*, to thus kill *Salmonella Typhimurium*.

Yet another objective of the present invention is to provide a disinfectant for preventing and treating diseases caused by *Salmonella Typhimurium* using the composition described above.

A further objective of the present invention is to provide a drinking-water additive for preventing and treating diseases caused by *Salmonella Typhimurium* using the composition described above.

Still a further objective of the present invention is to provide a feed additive effective upon feeding by preventing and treating diseases caused by *Salmonella Typhimurium* using the composition described above.

Technical Solution

The present invention provides a *Siphoviridae* bacteriophage STP-2 (Accession number: KCTC 12853BP) isolated from nature, which has the ability to specifically kill *Salmonella Typhimurium* and has the genome represented by SEQ ID NO: 1, and a method of preventing and treating diseases caused by *Salmonella Typhimurium* using a composition containing the same as an active ingredient.

The bacteriophage STP-2 was isolated by the present inventors and then deposited under the Budapest Treaty on the International Procedure at the Korea Collection for Type Cultures, Korea Research Institute of Bioscience and Biotechnology (KRIBB), 125 Gwahak-ro, Yuseong-gu, Daijeon 305-806, Republic of Korea; the deposit was made on Jun. 23, 2015 (Accession number: KCTC 12853BP).

In addition, the present invention provides a disinfectant, a drinking-water additive, and a feed additive applicable for the prevention and treatment of diseases caused by *Salmonella Typhimurium*, which contain the bacteriophage STP-2 as an active ingredient.

Since the bacteriophage STP-2 contained in the composition of the present invention kills *Salmonella Typhimurium* effectively, it is effective in the prevention (prevention of infection) and treatment (treatment of infection) of diseases caused by *Salmonella Typhimurium*. Therefore, the composition of the present invention is capable of being utilized for the prevention and treatment of diseases caused by *Salmonella Typhimurium*.

As used herein, the terms "prevention" and "prevent" refer to (i) prevention of *Salmonella Typhimurium* infection and (ii) inhibition of the development of diseases caused by a *Salmonella Typhimurium* infection.

As used herein, the terms "treatment" and "treat" refer to all actions that (i) inhibit diseases caused by *Salmonella Typhimurium* and (ii) alleviate the pathological condition of diseases caused by *Salmonella Typhimurium*.

As used herein, the terms "isolate", "isolating", and "isolated" refer to actions that isolate bacteriophages from nature by using diverse experimental techniques and that secure characteristics that can distinguish the bacteriophage of the present invention from others, and further include the action of proliferating the bacteriophage of the present invention using bioengineering techniques so that the bacteriophage is industrially applicable.

The pharmaceutically acceptable carrier included in the composition of the present invention is typically used for the preparation of a pharmaceutical formulation, and examples thereof include lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but are not limited thereto. The composition of the present invention may further include lubricants, wetting agents, sweeteners, flavors, emulsifiers, suspension agents, and preservatives, in addition to the above components.

The bacteriophage STP-2 is contained as an active ingredient in the composition of the present invention. The bacteriophage STP-2 is contained at a concentration from $1\times10^1$ pfu/ml to $1\times10^{30}$ pfu/ml or $1\times10^1$ pfu/g to $1\times10^{30}$ pfu/g, and preferably at a concentration from $1\times10^4$ pfu/ml to $1\times10^{15}$ pfu/ml or $1\times10^4$ pfu/g to $1\times10^{15}$ pfu/g.

The composition of the present invention may be formulated using a pharmaceutically acceptable carrier and/or excipient in accordance with a method that may be easily carried out by those skilled in the art to which the present invention belongs, in order to prepare the same in a unit dosage form or insert the same into a multi-dose container. Here, the formulation may be provided in the form of a solution, a suspension, or an emulsion in an oil or aqueous medium, or in the form of an extract, a powder, a granule, a tablet, or a capsule, and may additionally contain a dispersant or a stabilizer.

The composition of the present invention may be provided in the form of a disinfectant, a drinking-water additive or a feed additive depending on the purpose of use thereof, without limitation thereto. In order to improve the effectiveness thereof, bacteriophages that confer antibacterial activity against other bacterial species may be further included in the composition of the present invention. In addition, other kinds of bacteriophages that have antibacterial activity against *Salmonella Typhimurium* may be further included in the composition of the present invention. These bacteriophages may be combined appropriately so as to maximize the antibacterial effects thereof, because their antibacterial activities against *Salmonella Typhimurium* may vary from the aspects of antibacterial strength or antibacterial spectrum.

Advantageous Effects

According to the present invention, the method of preventing and treating diseases caused by *Salmonella Typhimurium* using the composition containing the bacteriophage STP-2 as an active ingredient can have the advantage of very high specificity for *Salmonella Typhimurium*, compared to conventional methods based on existing antibiotics. This means that the composition can be used for preventing and treating diseases caused by *Salmonella Typhimurium* without affecting useful commensal bacteria, and has fewer side effects attributable to the use thereof. Typically, when antibiotics are used, commensal bacteria are also harmed, ultimately lowering the immunity of animals and thus causing various side effects owing to the use thereof. Meanwhile, in the case of various bacteriophages exhibiting antibacterial activity against the same bacterial species, the antibacterial effects of the bacteriophages are different with regard to antibacterial strength or antibacterial spectrum [the range of various bacterial strains belonging to *Salmonella Typhimurium* across which antibacterial activity of bacteriophages is exhibited, given that bacteriophages typically exert antibacterial activity against some bacterial strains belonging to the same bacterial species, that is, susceptibility to bacteriophages varies even among individual bacterial strains belonging to the same bacterial species]. Accordingly, the present invention can provide antibacterial activity against *Salmonella Typhimurium* different from that of other bacteriophages acting on *Salmonella Typhimurium*. This provides a great difference in effectiveness when application to industrial fields.

DESCRIPTION OF DRAWINGS

FIG. 3 shows the deposit information under the Budapest Treaty on the International Recognition of the Deposit of Microorganisms For the Purposes of Patent Procedure.

MODE FOR INVENTION

A better understanding of the present invention will be given through the following examples, which are merely set forth to illustrate the present invention, and are not to be construed as limiting the scope of the present invention.

Example 1: Isolation of Bacteriophage Capable of Killing *Salmonella Typhimurium*

Samples collected from nature were used to isolate a bacteriophage capable of killing *Salmonella Typhimurium*. Here, the *Salmonella Typhimurium* bacteria used for the bacteriophage isolation were obtained from the American Type Culture Collection (ATCC) (ATCC14028).

The procedure for isolating the bacteriophage is specified below. The collected sample was added to a TSB (Tryptic Soy Broth) culture medium (casein digest, 17 g/L; soybean digest, 3 g/L; dextrose, 2.5 g/L; NaCl, 5 g/L; dipotassium phosphate, 2.5 g/L) inoculated with *Salmonella Typhimurium* at a ratio of 1/1,000, followed by shaking culture at 37° C. for 3 to 4 hr. After completion of the culture, centrifugation was performed at 8,000 rpm for 20 min and the supernatant was recovered. The recovered supernatant was inoculated with *Salmonella Typhimurium* at a ratio of 1/1000, followed by shaking culture at 37° C. for 3 to 4 hr. When the bacteriophage was included in the sample, the above procedure was repeated a total of 5 times in order to sufficiently increase the number (titer) of bacteriophages. After the procedure was repeated 5 times, the culture solution was centrifuged at 8,000 rpm for 20 min. After centrifugation, the recovered supernatant was filtered using a 0.45 µm filter. The filtrate thus obtained was used in a typical spot assay for examining whether or not a bacteriophage capable of killing *Salmonella Typhimurium* was included therein.

The spot assay was performed as follows. A TSB culture medium was inoculated with *Salmonella Typhimurium* at a ratio of 1/1,000, followed by shaking culture at 37° C. overnight. 3 ml ($OD_{600}$ of 1.5) of the *Salmonella Typhimurium* culture solution prepared as described above was spread on a TSA (Tryptic Soy Agar) plate medium (casein digest, 15 g/L; soybean digest, 5 g/L; NaCl, 5 g/L; agar, 15 g/L). The plate was allowed to stand on a clean bench for about 30 min to dry the spread solution. After drying, 10 µl of the filtrate prepared as described above was spotted onto the plate medium on which *Salmonella Typhimurium* was spread, and was then allowed to stand for about 30 min to dry. After drying, the plate medium that was subjected to spotting was subjected to stationary culture at 37° C. for one day, and then examined for the formation of a clear zone at the position at which the filtrate was dropped. In the case in which the filtrate generated a clear zone, it was judged that a bacteriophage capable of killing *Salmonella Typhimurium* was included therein. Through the above examination, it was possible to obtain a filtrate containing a bacteriophage having the ability to kill *Salmonella Typhimurium*.

Figure 1:
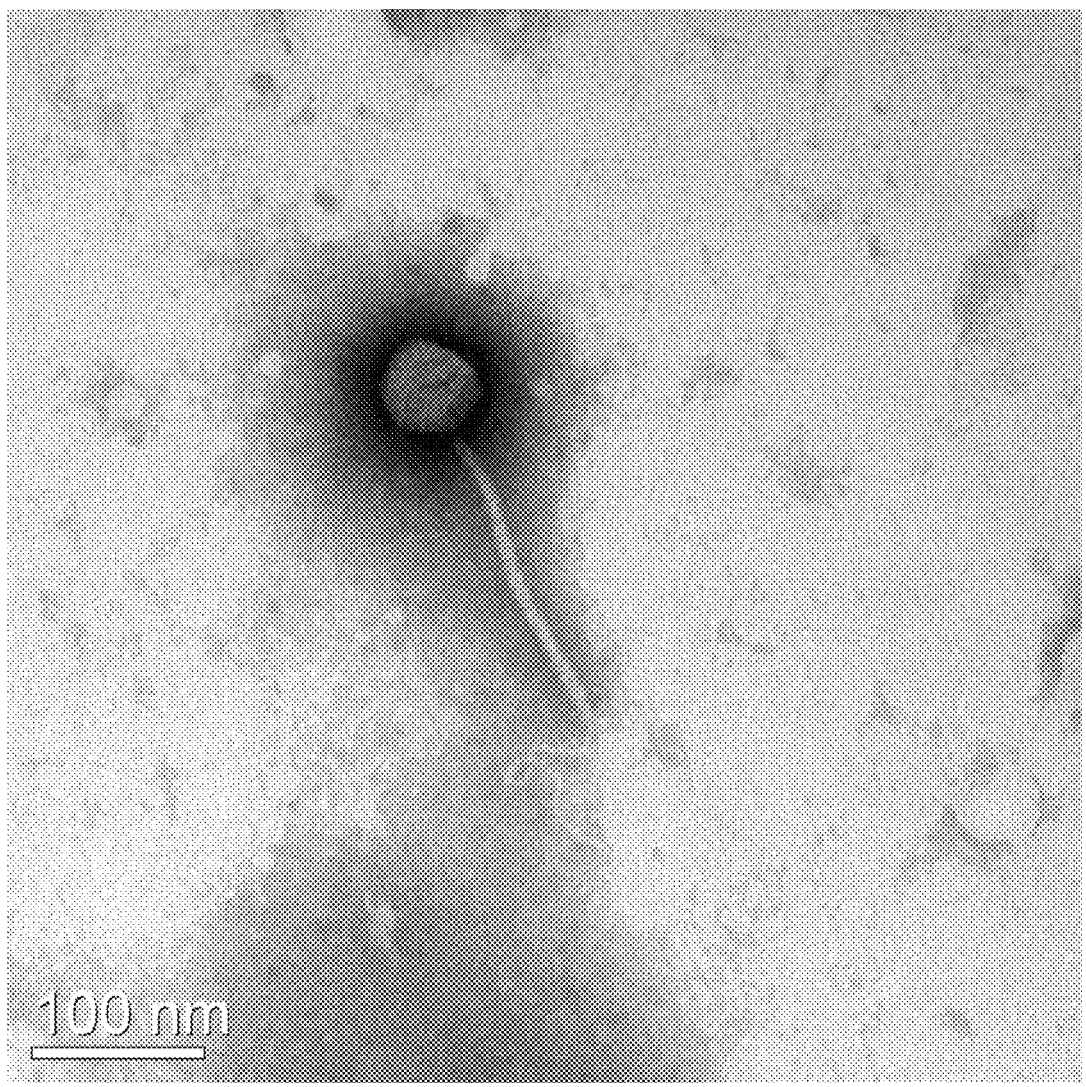
FIG. 1 shows an electron micrograph of the bacteriophage STP-2.

The pure bacteriophage was isolated from the filtrate confirmed to have the bacteriophage capable of killing *Salmonella Typhimurium*. A typical plaque assay was used to isolate the pure bacteriophage. Specifically, a plaque formed in the course of the plaque assay was recovered using a sterilized tip, added to the *Salmonella Typhimurium* culture solution, and then cultured at 37° C. for 4 to 5 hr. Thereafter, centrifugation was performed at 8,000 rpm for 20 min to obtain a supernatant. The supernatant thus obtained was added with the *Salmonella Typhimurium* culture solution at a volume ratio of 1/50 and then cultured at 37° C. for 4 to 5 hr. In order to increase the number of bacteriophages, the above procedure was repeated at least 5 times, after which centrifugation was performed at 8,000 rpm for 20 min to obtain a final supernatant. A plaque assay was performed again using the supernatant thus obtained. In general, isolation of a pure bacteriophage is not completed through a single iteration of a procedure, so the above procedure was repeated using the plaque formed above. After at least 5 repetitions of the procedure, the solution containing the pure bacteriophage was obtained. The procedure for isolation of the pure bacteriophage was repeated until the generated plaques became generally similar to each other with regard to size and morphology. Additionally, final isolation of the pure bacteriophage was confirmed using electron microscopy. The above procedure was repeated until isolation of the pure bacteriophage was confirmed using electron microscopy. The electron microscopy was performed according to a typical method. Briefly, the solution containing the pure bacteriophage was loaded on a copper grid, followed by negative staining with 2% uranyl acetate and drying. The morphology thereof was then observed using a transmission electron microscope. The electron micrograph of the pure bacteriophage that was isolated is shown in FIG. 1. Based on the morphological characteristics thereof, the novel bacteriophage that was isolated above was confirmed to be a *Siphoviridae* bacteriophage.

The solution containing the pure bacteriophage confirmed above was subjected to the following purification process. The solution containing the pure bacteriophage was added with the *Salmonella Typhimurium* culture solution at a volume ratio of 1/50, based on the total volume of the solution, and then cultured for 4 to 5 hr. Thereafter, centrifugation was performed at 8,000 rpm for 20 min to obtain a supernatant. This procedure was repeated a total of times in order to obtain a solution containing a sufficient number of bacteriophages. The supernatant obtained from the final centrifugation was filtered using a 0.45 µm filter, followed by a typical polyethylene glycol (PEG) precipitation process. Specifically, 100 ml of the filtrate was added with 10% PEG 8000 and 0.5 M NaCl, allowed to stand at 4° C. for 2 to 3 hr, and then centrifuged at 8,000 rpm for 30 min to obtain a bacteriophage precipitate. The resulting bacteriophage precipitate was suspended in 5 ml of a buffer (10 mM Tris-HCl, 10 mM MgSO$_4$, 0.1% gelatin, pH 8.0). The resulting material may be referred to as a bacteriophage suspension or bacteriophage solution.

The bacteriophage purified as described above was collected, was named bacteriophage STP-2, and was then deposited under the Budapest Treaty on the International Procedure at the Korea Collection for Type Cultures, Korea Research Institute of Bioscience and Biotechnology (KRIBB), 125 Gwahak-ro, Yuseong-gu, Daijeon 305-806, Republic of Korea; the deposit was made on Jun. 23, 2015 (Accession number: KCTC 12853BP).

Example 2: Separation and Sequence Analysis of Genome of Bacteriophage STP-2

The genome of the bacteriophage STP-2 was separated as follows. The genome was separated from a bacteriophage suspension obtained using the same method as described in Example 1. First, in order to eliminate DNA and RNA of *Salmonella Typhimurium* included in the suspension, 10 ml of the bacteriophage suspension was added with 200 U of each of DNase I and RNase A and then allowed to stand at 37° C. for 30 min. After being allowed to stand for 30 min, in order to stop the DNase I and RNase A activity, 500 µl of 0.5 M ethylenediaminetetraacetic acid (EDTA) was added thereto, and the resulting mixture was then allowed to stand for 10 min. In addition, the resulting mixture was again allowed to stand at 65° C. for 10 min, and 100 µl of proteinase K (20 mg/ml) was then added thereto so as to break the outer wall of the bacteriophage, followed by reaction at 37° C. for 20 min. Thereafter, 500 µl of 10% sodium dodecyl sulfate (SDS) was added thereto, followed by reaction at 65° C. for 1 hr. After the reaction for 1 hr, the resulting reaction solution was added with 10 ml of a mixed solution of phenol, chloroform and isoamyl alcohol at a component ratio of 25:24:1 and then mixed thoroughly. Then, the resulting mixture was centrifuged at 13,000 rpm for 15 min to thus separate layers. Among the separated layers, the upper layer was selected, added with isopropyl alcohol at a volume ratio of 1.5, and centrifuged at 13,000 rpm for 10 min in order to precipitate the genome. The precipitate was recovered and washed by addition with 70% ethanol, then centrifuged at 13,000 rpm for 10 min. The washed precipitate was recovered, dried in a vacuum and then dissolved in 100 µl of water. This procedure was repeated to thus obtain a large amount of the genome of the bacteriophage STP-2.

The genome thus obtained was subjected to next-generation sequencing analysis using a Pac-bio sequencer from the National Instrumentation Center for Environmental Management, Seoul National University, and then information on the sequence of the genome of bacteriophage STP-2 was obtained. The finally analyzed genome of the bacteriophage STP-2 had a size of 59,043 bp, and the sequence of the whole genome is represented by SEQ ID NO: 1.

The homology (similarity) of the bacteriophage STP-2 genomic sequence obtained above with previously reported bacteriophage genomic sequences was investigated using BLAST on the web. Based on the results of BLAST investigation, the genomic sequence of the bacteriophage STP-2 was identified to have relatively high homology with the sequence of the *Salmonella* bacteriophage iEPS5 (GenBank Accession number: KC677662.1) (identity: 99%). However, the bacteriophage STP-2 has a circular genome and the *Salmonella* bacteriophage iEPS5 has a linear genome. Furthermore, the number of open reading frames (ORFs) on the bacteriophage STP-2 genome was 102, whereas the *Salmonella* bacteriophage iEPS5 was found to have 73 open reading frames, based on which these two bacteriophages were evaluated to be genetically different. The difference in genetic characteristics between these two bacteriophages can indicate that there are external and functional differences in various characteristics expressed in various ways between the two bacteriophages. Furthermore, the difference between these two bacteriophages also indicates that there is a Therefore, it can be concluded that the bacteriophage STP-2 is a novel bacteriophage different from previously reported bacteriophages. Moreover, since the antibacterial strength and spectrum of bacteriophages typically vary depending on the type of bacteriophage, it is considered that the bacteriophage STP-2 can provide antibacterial activity different from that of any other previously reported bacteriophage.

Example 3: Evaluation of Ability of Bacteriophage STP-2 to Kill *Salmonella Typhimurium*

Figure 2:
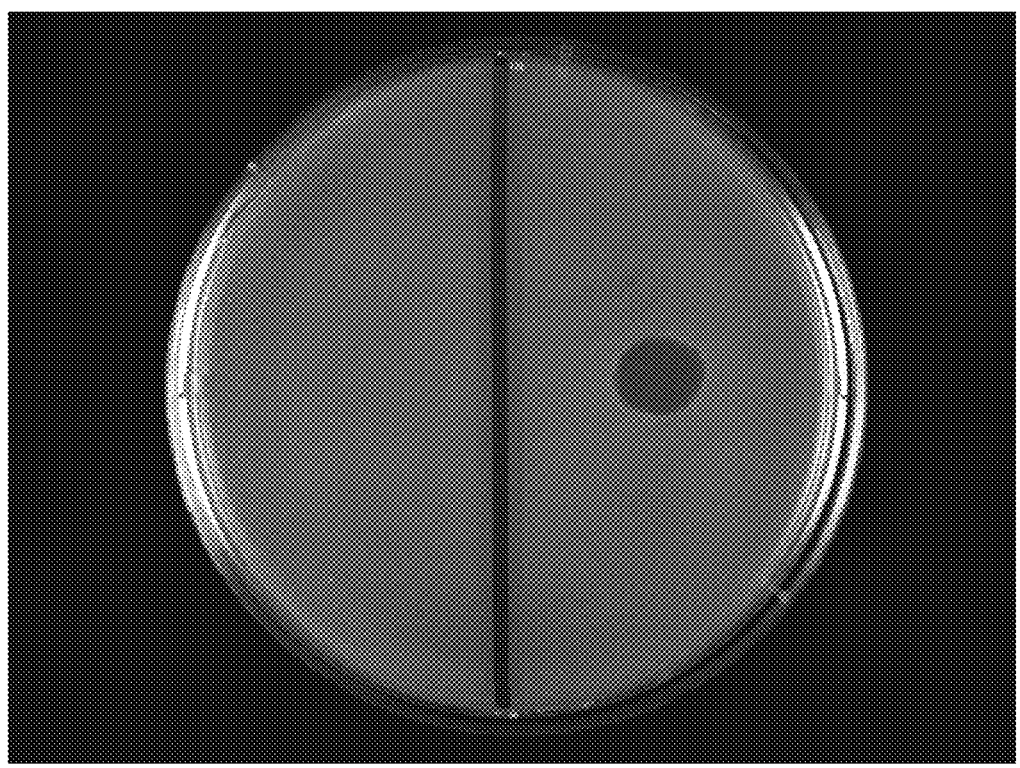
FIG. 2 shows the results of an experiment on the ability of the bacteriophage STP-2 to kill *Salmonella Typhimurium*, in which, based on the center line of the plate medium, the left side shows the results obtained using only a buffer not containing bacteriophage STP-2, and the right side shows the results obtained using a solution containing bacteriophage STP-2, in which the clear zone, which is observed at the right side, is a plaque formed due to lysis of the target bacteria by the action of bacteriophage STP-2.

The ability of the isolated bacteriophage STP-2 to kill *Salmonella Typhimurium* was evaluated. In order to evaluate the killing ability, the formation of clear zones was observed using a spot assay in the same manner as described in Example 1. A total of 10 strains that had been isolated and identified as *Salmonella Typhimurium* by the present inventors or obtained from ATCC were used as *Salmonella Typhimurium* strains for evaluation of killing ability. The bacteriophage STP-2 had the ability to kill a total of 9 strains, including ATCC14028, among 10 strains of *Salmonella Typhimurium*, which was the experimental target. The representative experimental result is shown in FIG. 2. Meanwhile, the ability of the bacteriophage STP-2 to kill *Bordetella bronchiseptica*, *Enterococcus faecalis*, *Enterococcus faecium*, *Streptococcus mitis*, *Streptococcus uberis* and *Pseudomonas aeruginosa* was also measured. Consequently, the bacteriophage STP-2 was found not to have the ability to kill these microorganisms.

Therefore, it can be concluded that the bacteriophage STP-2 has strong ability to kill *Salmonella Typhimurium* and can exhibit antibacterial effects against many *Salmonella Typhimurium* strains, indicating that the bacteriophage STP-2 can be used as an active ingredient of a composition for preventing and treating diseases caused by *Salmonella Typhimurium*.

Example 4: Experiment for Prevention of *Salmonella Typhimurium* Infection Using Bacteriophage STP-2

100 μl of a bacteriophage STP-2 solution at a concentration of $1\times10^8$ pfu/ml was added to a tube containing 9 ml of a TSB culture medium. To another tube containing 9 ml of a TSB culture medium, only the same amount of TSB culture medium was further added. A *Salmonella Typhimurium* culture solution was then added to each tube so that absorbance reached about 0.5 at 600 nm. After the addition of *Salmonella Typhimurium*, the tubes were transferred to an incubator at 37° C., followed by shaking culture, during which the growth of *Salmonella Typhimurium* was observed. As shown in Table 1 below, it was observed that the growth of *Salmonella Typhimurium* was inhibited in the tube to which the bacteriophage STP-2 solution was added, whereas the growth of *Salmonella Typhimurium* was not inhibited in the tube t the bacteriophage solution was not added.

TABLE 1

Growth inhibition of *Salmonella* Typhimurium

| Classification | $OD_{600}$ absorbance value | | |
|---|---|---|---|
| | 0 min after culture | 60 min after culture | 120 min after culture |
| Not added with bacteriophage solution | 0.5 | 0.9 | 1.6 |
| Added with bacteriophage solution | 0.5 | 0.2 | 0.1 |

The above results show that the bacteriophage STP-2 of the present invention not only inhibits the growth of *Salmonella Typhimurium* but also has the ability to kill *Salmonella Typhimurium*. Therefore, it is concluded that the bacteriophage STP-2 can be used as an active ingredient in a composition for preventing diseases caused by *Salmonella Typhimurium*.

Example 5: Animal Testing for Prevention of Disease Caused by *Salmonella Typhimurium* Using Bacteriophage STP-2

The preventive effect of the bacteriophage STP-2 on diseases caused by *Salmonella Typhimurium* was evaluated using weaning pigs. Twenty 25-day-old weaning pigs were divided into a total of 2 groups (10 pigs per group) and reared separately in experimental pig-rearing rooms (1.1 m×1.0 m), and an experiment was performed for 14 days. The surrounding environment was controlled using a heater, and the temperature and humidity in the pig rooms were maintained constant, and the pig room floors were washed every day. A feed containing $1\times10^8$ pfu/g of bacteriophage STP-2 was provided to pigs in an experimental group (administered with feed containing the bacteriophage) in a typical feeding manner starting from the beginning of the experiment until the end of the experiment. For comparison therewith, a feed having the same composition but not containing bacteriophage STP-2 was provided to pigs in a control group (administered with feed not containing the bacteriophage) in the same feeding manner starting from the beginning of the experiment until the end of the experiment. For 2 days from the seventh day after the start of the experiment, the feed was further added with $1\times10^8$ cfu/g of *Salmonella Typhimurium* and then provided to all of the pigs in the experimental group (administered with feed containing the bacteriophage) and the control group (administered with feed not containing the bacteriophage) twice a day, thereby inducing infection with *Salmonella Typhimurium*. The detected level of *Salmonella Typhimurium* in the feces of all test animals was examined daily from the date of feeding with the feed containing *Salmonella Typhimurium* (from the seventh day after the start of the experiment), and the severity of diarrhea of the pigs was also examined.

The detection of *Salmonella Typhimurium* in feces was carried out as follows. The fecal sample was spread on a *Salmonella-Typhimurium*-selective medium (RAMBACH® agar; Merck) and then cultured at 37° C. for 18 to 24 hr. Among the resulting colonies, colonies presumed to be *Salmonella Typhimurium* were isolated. The colonies thus obtained were used as samples and subjected to polymerase chain reaction (PCR) specific to *Salmonella Typhimurium*, and thus whether or not the corresponding colonies were *Salmonella Typhimurium* was finally confirmed.

The occurrence of diarrhea was determined through comparison with a diarrhea index. The diarrhea index was measured according to a commonly used Fecal Consistency (FC) score (normal: 0, soft stool: 1, loose diarrhea: 2, severe diarrhea: 3).

The results thereof are shown in Tables 2 and 3 below.

TABLE 2

Results of detection of *Salmonella Typhimurium* (mean)

| Classification | Number of colonies of *Salmonella Typhimurium* detected per plate | | | | | | | |
|---|---|---|---|---|---|---|---|---|
| | D7 | D8 | D9 | D10 | D11 | D12 | D13 | D14 |
| Control group (administered with feed not containing bacteriophage) | 24 | 21 | 18 | 17 | 16 | 17 | 14 | 14 |
| Experimental group (administered with feed containing bacteriophage) | 12 | 8 | 7 | 3 | 1 | 0 | 0 | 0 |

TABLE 3

| Classification | Diarrhea index | | | | | | | |
|---|---|---|---|---|---|---|---|---|
| | D7 | D8 | D9 | D10 | D11 | D12 | D13 | D14 |
| Control group (administered with feed not containing bacteriophage) | 1.6 | 1.8 | 2.0 | 1.6 | 1.4 | 1.5 | 1.2 | 1.2 |
| Experimental group (administered with feed containing bacteriophage) | 0.6 | 0.4 | 0.2 | 0 | 0 | 0 | 0 | 0 |

As is apparent from the above results, it can be confirmed that the bacteriophage STP-2 of the present invention was very effective in the prevention of diseases caused by *Salmonella Typhimurium*.

Example 6: Treatment of Disease Caused by *Salmonella Typhimurium* Using Bacteriophage STP-2

The therapeutic effect of the bacteriophage STP-2 on diseases caused by *Salmonella Typhimurium* was evaluated as follows. 2 groups of forty 2-day-old chicks per group were prepared and, reared separately, and an experiment was performed for 14 days. For 3 days from the fifth day after the start of the experiment, a feed containing $1 \times 10^7$ cfu/g of *Salmonella Typhimurium* was provided in a typical feeding manner. From the next day after the feeding with the feed containing *Salmonella Typhimurium* for 3 days (from the eighth day after the start of the experiment), a feed containing $1 \times 10^8$ pfu/g of bacteriophage STP-2 was provided to chicks in an experimental group (administered with feed containing the bacteriophage) in a typical feeding manner. For comparison, a feed having the same composition but not containing bacteriophage STP-2 was provided to chicks in a control group (administered with feed not containing the bacteriophage) in the same feeding manner. From the eighth day after the start of the experiment, the number of *Salmonella Typhimurium* bacteria in the feces of the test animals was measured. A *Salmonella-Typhimurium*-selective medium (RAMBACH© agar, Merck) was used to prevent interference due to contamination with other bacteria in the measurement of the number of *Salmonella Typhimurium* bacteria in this example. The sample was spread on the selective medium and then cultured at 37° C. for 18 to 24 hr. The colonies presumed to be *Salmonella Typhimurium* were isolated from the cultured selective medium, after which *Salmonella Typhimurium* was identified through polymerase chain reaction (the case where the number of colonies identified as *Salmonella Typhimurium* through polymerase chain reaction is $10^2$ cfu/ml or more=2, the case where the number of colonies identified as *Salmonella Typhimurium* through polymerase chain reaction is $10^1$ to $10^2$ cfu/ml=1, and the case where the number of colonies identified as *Salmonella Typhimurium* through polymerase chain reaction is 100 to $10^1$ cfu/ml=0). For reference, *Salmonella Typhimurium* bacteria were observed in the feces of both groups from the day after the end of administration of the feed containing *Salmonella Typhimurium* bacteria (from the eighth day after the start of the experiment), indicating that forced infection was well induced. The results of measurement of the number of *Salmonella Typhimurium* bacteria are shown in Table 4 below.

TABLE 4

| Days | Results of measurement of number of *Salmonella Typhimurium* bacteria (mean) | | | | | | |
|---|---|---|---|---|---|---|---|
| | D8 | D9 | D10 | D11 | D12 | D13 | D14 |
| Control group (administered with feed not containing bacteriophage) | 1.2 | 1.2 | 1.0 | 1.1 | 1.0 | 1.1 | 1.0 |
| Experimental group (administered with feed containing bacteriophage) | 0.3 | 0.2 | 0.2 | 0 | 0 | 0 | 0 |

As is apparent from the above results, it can be confirmed that the bacteriophage STP-2 of the present invention was very effective in the treatment of diseases caused by *Salmonella Typhimurium*.

Example 7: Preparation of Feed Additive and Feed

Feed additives were prepared using a bacteriophage STP-2 solution so that bacteriophage STP-2 was contained in an amount of $1 \times 10^8$ pfu per gram of the feed additive. The feed additives were prepared in a manner in which the bacteriophage solution was added with maltodextrin (50%, w/v) and then freeze-dried, followed by final pulverization into a fine powder. In the above preparation procedure, the drying process may be embodied as drying under reduced pressure, drying with heat, or drying at room temperature. In order to prepare the control for comparison, the feed additives not containing the bacteriophage were prepared using the buffer (10 mM Tris-HCl, 10 mM $MgSO_4$, 0.1% gelatin, pH 8.0) used in the preparation of the bacteriophage solution, in lieu of the bacteriophage solution.

Each of the two kinds of feed additives thus prepared was mixed with a poultry feed at a weight ratio of 1,000, thus finally obtaining two kinds of feed.

Example 8: Preparation of Drinking-Water Additive and Disinfectant

A drinking-water additive and a disinfectant were prepared in the same manner because they differ only in utilization and are the same in dosage form. The drinking-water additive (or disinfectant) was prepared using a bacteriophage STP-2 solution so that the bacteriophage STP-2 was contained in an amount of $1 \times 10^9$ pfu per ml of the drinking-water additive (or disinfectant). In the method of preparing the drinking-water additive (or disinfectant), the bacteriophage STP-2 solution was added so that the bacteriophage STP-2 was contained in an amount of $1 \times 10^9$ pfu per ml of the buffer used in the preparation of the bacteriophage solution, and mixing was sufficiently performed. In order to prepare the control for comparison, the buffer used in the preparation of the bacteriophage solution was used without change as a drinking-water additive (or disinfectant) not containing the bacteriophage.

The two kinds of drinking-water additives (or disinfectants) thus prepared were diluted with water at a volume ratio of 1,000, thus obtaining final drinking water or disinfectants.

Example 9: Confirmation of Feeding Effect on Chicken Farming

The improvement in chicken farming as the result of feeding was evaluated using the feed, drinking water and disinfectant prepared in Examples 7 and 8. In particular, the present evaluation was focused on mortality ratio. A total of 120 2-day-old chicks were divided into three groups, each including 40 chicks (group A: fed with the feed, group B: fed with the drinking water, and group C: treated with the disinfectant), and an experiment was performed for four weeks. Each group was divided into subgroups each including 20 chicks, and the subgroups were classified into a subgroup to which the bacteriophage STP-2 was applied (subgroup-①) and a subgroup to which the bacteriophage was not applied (subgroup-②). In the present experiment, the chicks were raised separately in individual subgroups. The subgroups were classified and named as shown in Table 5 below.

TABLE 5

Subgroup classification and expression in chicken-feeding experiment

| Application | Subgroup classification and expression | |
|---|---|---|
| | Bacteriophage STP-2 is applied | Bacteriophage is not applied |
| Group fed with feed | A-① | A-② |
| Group fed with drinking water | B-① | B-② |
| Group treated with disinfectant | C-① | C-② |

In the case of provision of the feed, the feed prepared in Example 7 was provided in a typical feeding manner, as shown in Table 5, and the drinking water prepared in Example 8 was provided in a typical feeding manner, as shown in Table 5. In the case of disinfection, the disinfection was carried out alternately with conventional disinfection 3 times a week. Disinfection using a typical disinfectant was not performed on the day on which the disinfectant of the present invention was sprayed. The experimental results thereof are shown in Table 6 below.

TABLE 6

Mortality in chicken-feeding experiment

| Group | Mortality (%) |
|---|---|
| A-① | 0 |
| A-② | 45 |
| B-① | 5 |
| B-② | 45 |
| C-① | 5 |
| C-② | 45 |

The above results indicate that the provision of the feed and the drinking water prepared according to the present invention and the disinfection according to the present invention were effective at reducing mortality ratio upon chicken farming. Therefore, it is concluded that the composition of the present invention is effective when used to feed chickens.

While the present invention has been particularly shown and described with reference to exemplary embodiments thereof, those skilled in the art will appreciate that the specific description is only a preferred embodiment, and that the scope of the present invention is not limited thereto. It is therefore intended that the scope of the present invention be defined by the claims appended hereto and their equivalents.

Accession Number

Name of Depositary Authority: KCTC
Accession number: KCTC 12853BP
Accession date: 20150623

The invention claimed is:

1. A method of preventing and treating a disease caused by *Salmonella Typhimurium*, comprising:
   administering to an animal other than a human a composition comprising, as the active ingredient, a *Siphoviridae* bacteriophage STP-2 which has an ability to kill *Salmonella Typhimurium* and a genome represented by a sequence as set forth in SEQ ID NO: 1, and is deposited as accession number KCTC 12853BP.

2. The method of claim 1, wherein the composition is administered to the animal other than the human in a form of a feed additive, a drinking-water additive or a disinfectant.

* * * * *

SEQUENCE LISTING

```
<160> NUMBER OF SEQ ID NOS: 1

<210> SEQ ID NO 1
<211> LENGTH: 59043
<212> TYPE: DNA
<213> ORGANISM: Bacteriophage STP-2

<400> SEQUENCE: 1
atcaaggtcg cgctggtgga tcatcttgtt aacgatggac aggtcggtca cgtcctcgat      60
cagcttcggc gttctcggca ggttttgagt ctgaatacgg cggccagccc aacggttcgt     120
gcggcttgcc ccggcgaatt gcagcgagaa gcggaatcgt ccatcttcgc cagccgcgtc     180
aatcatggtc tgatattttg acagggagtt tttcgcgcta ttcaggcgca tccgcagcac     240
gcggatcgca tccgggtcaa cgccgttttc atcggcttcg cgaatgacct tgttgacggt     300
gtcactgcga aggtcgctga acggatagcc gcgctctttg agccacggtg ttaactgcgc     360
cgggaattgg ggttgttcag gccagtgatg tcggccattt cttcgataat ctgcggtttg     420
```

```
cgcgcctctg cgagcgccag cgccgagtac gcgaattcgc ggtcaatcat cacgcctgta    480
tcgttgatga actgatccag cgcgtacatg tcccattcgg catccagaac cgggtaccgc    540
atcaggcggg ctttaatcgc cagttcggtt tcaacgtccc gcacgttata tttgcagaag    600
tgccaccagt cttccgggtc ggtcgcttca ttgcgccact caaacgggtt tttcttcgtg    660
acgcgctgcg gcttgctgaa caggtcgatc aggcgcttgc cttccgggtc tttcagtttc    720
tcttccggca agccgatctg cgtgccgacg gccagaaggt cgcccgcaaa gccgagcatg    780
tacgccagcg ccatcgtaca gcgccacgat ttatacggcg tcttgatgcc gagcacccgg    840
cgggtcatta cgcgttcgaa ctgcgcgtta aggcccact tctcgacggc cggtcttcca    900
gcgcttcacg cagttcgccg ggcaacttct ccctcggtg aaggtcgata tgctgcaccg    960
ctccgccatt gatagaccat cgcccatca gaattttagt cgattcgtcg ttcgaatatc    1020
ggtcgaatcc gttcgtttta aggttcaccc ggcttcggga ttcatagtcc agattaatgc    1080
aatcggtcac gttaacgctc ctgtatgaaa aagcccgca cgcggcgggc cttgtattac    1140
cgcccgaggg cgtacattac acttcgtctt cccaatcttc gtcttcatcc cacgcgtcgg    1200
acgtgtccac acgaccttca ccgaacggct cgtcgtcttt gcgtttcaga acggaaatca    1260
ggttggcgtt aacgcgtttg ccgaatttgt ttcctgcga ccacggacgg atgacaaccg    1320
acacccaaca accaccgtag atctcttcca gaatttcgga agaggtagtc aactcttcgc    1380
gctcgatgtt atacacatcc gggcgtttgc tttcgcgtgc ggagataacc cacatccctt    1440
cgcattccgg tttatccgga aaatcggtat caccgtcttt gatgaacaac atggacgggg    1500
cgactttcag cgcgcctgtc ttgtggttct tcttggtgac ttcgatctgc tcacggatga    1560
ttttctcgat ctcgccgtgg ctgtctttcg gcatcaaaag cgtcagcgag tatttcggct    1620
cgccgccgtc ttcaccgccg tacggcttat cgaggtgcgg gtaagaagca cgtacgttag    1680
aaatcttgat gtgaccagat ttgtacagca cgccattctt gactttttc gcagggacta    1740 atttctcggc catcttaata tcctcggttt actgttttac gggtttactt tctacggttt    1800
tacgggttta cacttcgtca tcatcttcgt cgtcccacgc cccggaatac ttgccgtcca    1860
gtggtggccg cttatcggtc agcggtgcca gtgtcggctt gccttccggc ttgtagacga    1920
tccccgcgat gatgttcggc gcgccagccc gggacacgcc caattcatcc ctaagcactt    1980
cttccatctg cgccggggta cgcagtttgc gttcgatgta cttgtcctcg tcaatatcga    2040
ggaaccggaa cagcgcgatc gcatctttct cattggcgaa tttacggttt gtccgcgact    2100
ccaccagctt ttgacccggt accttctcgc cgttcattgc gcggcgttcc agttcgaagt    2160
caaggcgcga gaaccagttt tcgaccacct tgcggtatgg caggatcttc gccatctgct    2220
cggttgtcag gttccgaac tgcgcccgcc ggaacttata ttcctgcgcc agcgcatcac    2280
gcaatactga catttcttcc tcccgaatt cagcttcaag gaattccacg tccccgccca    2340
ctgcgcattc catcatgtac gctatcgctg cgcagttatg cgctgccgg caaaagcgac    2400 acccttcag ggatgcgcgg cgcggcgcgg taaggctcca tgccgctgca attcgctccc    2460
gggcatactc cgcgaactct aacaattcgt caatcgtgat ttcccacgta tcgaaatggt    2520
cgagcctcgg ctgcgcgatc cggatgacaa tacggtcaaa ctcgtattca tctgcgaaag    2580
cgcggtacgc accgtacgcg taaagtagcg cctgcgggtt cccttccgcg aaaacctgaa    2640
cgccagtccc gtatttcagg tcggtcacga tcaaggttcg gtcgcggatg atgatattat    2700
ccgccgttcc gccctgagcg acaaactcga tcgggtcttc gtcaggttca tccgggttcg    2760
```

```
ctcgcggcat caggtcggta aaccagaccc ggatttccgt gaacatttca ccctcttcaa    2820
atcggcacca gtccacgtac tcctgaaccg agtcgagcat tgaccgcgta atcgggatgt    2880
catggctgac accgccttcc gtgatcgtct cgactgtacc gattaaatgg gttggccgga    2940
catccgttcg cagccattgt tcggcgattc cgtgggccac cgtgccttcc gccgcctcgt    3000
agatggtttc gtcatgctca aaaagcccgg ctatcaggct tccagaacat gcgatccaac    3060
gcgctgacgc agaaggcgcg aagattgagt ggccgccacc gccgaattcc cgcatgatgc    3120
ggactaacag tgacttacta ctcattcgga tacgccttta tcgcattgag gaatcggtgt    3180
tcgccgactc gctcaatcgt cgctaccaat gccctagcgc ctgccccgct gtaattattg    3240
cggcctgcgt taaagcgagt cttcgccacg tcgtcccacc agacgtcgca cactcgatag    3300
cccgatgcag catgggttac gagcagcggc gcttctagtt tcgaaacagg tgaagtaact    3360
ctgaacagca catcgcgatc accgatttga aaacgaaact ccgcccaagt gcgcgcgaga    3420
actgcgccgc cggatgttgc tacgttggtg aaagtaatgc tggtcacaat tgcctctccg    3480
ttggtgtgaa aaacggcccc cgaagggagc cgatgcgggg cgaaagatta acgtcgtct    3540 tcttcgccgt taccgccttc atcttttttca gccagtttgg cttcacacat ttcgacgatt    3600
tcgtcgaagt gttcttcctt cgcttccgcg actttggcga ggccgaagtg tgcggtgatt    3660
ttcttggctt ccggcgcgcc gaacgcgtct ttaaccgcaa cgacagccgc gactacttcg    3720
tctttggtgt gtttaggctt gaccgcttta gtttcggttt tacctgcacc gccttTCGCG    3780
ccgcccttag caccgccttt ggtggtagtg gtggtttttt cagtggtttc gctaccagcg    3840
tcagcggaag tgttcaccgc gccgcctttc agtgctgcca gaacgccttc cagcagggtg    3900 ttagttttt gttgttcagc cagcagttgt tcgaagatac cagacataat tttctactcc    3960
gttaagtgtt taaaggtcg tgtcgtgttg acgggatgaa gtatggccca aacgccgaat    4020
aactgtcaaa cacttttttc gaaattttttt gattaggtac ctcaaagcct tgtattccgg    4080
acgtaagatg gttgcggtac ccgactaaat ggccagcttg acagattttac gggccggata    4140 tactatccgc aaatctataa cacgcacaca tgcgagggct tgggctatgc gatttccgaa    4200
atgggcttta aatgatgacc ggatgaaggt caaattccta atgacacaag cggcgttaga    4260
gatcgacccg aatgccagaa tggcggactt agcgaaggct gcgaaggtaa gctactcgac    4320
tcttttatgg gcgacgcaaa ataacgtatc gagcgccgtg gccgaaaaag tttgcagcgc    4380
ggtaccgctg accgggatcc gccccactgg ctgactaacc cttcttggat caaaactgac    4440
agcgaaacag gggaaatcct tgaatgaatt actggcaaga gtacggcgaa acgctttggg    4500
gaatgggtac accatcgtac ctatctacgc cccggacgcc gataagaagg gcgcgggtaa    4560
acgccccatc ggtaaggatt gggaacgaac cattaacgat aaggagcaga tccagcgttg    4620
ggcggaacgc ttcaccaaaa acggtattgg catcctgacc aaatacaccc cggccgtgga    4680
catcgacgtg tacgatgaag acgccgtggc gcatatgtcg gattgggtgc tggagaatgt    4740
tggccgcgcg ccttgtcgta tcggccggag ccaaagaaac ttttcctgtt cagatcggaa    4800
tcgccattct cgaaagtgaa gtccggcgtg tgggaagacg acttcggcca gcgccatgcg    4860
gttgaaatcc tcgccgacgg ccagcagttc gtcgcgtacg gtatccaccc ggacaccaac    4920
cgcgattatt actggctcga cgacgaaacc ccgctgaaca atgcggccga cttcgacctt    4980
gaagagatca gcctcgatac cgcgcgggaa attgctgcgg agtttgaccg ctacgccaaa    5040
gaacaaggct ggacgatggt caagcgcccg atgaacgggg acgaagccat cggaacggcg    5100
gacgaagagg attgggcggc aacggcgggt atccggaaat gggacggcac gtacgaagac    5160
```

```
cttcgcgatc tcgtcatgaa gtacccgaat ccggaagatt atgagaacta catcaaggtt    5220
ctggccgcgt tgcaaatctc ctgccgggat caggacgaag ccaagtcgat tgctcgcgaa    5280
tgggccatgc aggcgcacaa ctttgatgat ggtgatttcg agtacaaatg ggataagggc    5340
tttgcgcata acgcatcacg ccttgtaacc ctcggatcga tcatcaccga agtccgtgaa    5400
atcgagaaag ccgagcagga agagaaggcc atcgagtacc gcgaggcttt cgccgagtgt    5460
accgaagcaa atgactggaa tgcgtgggcc gaatccttca aaaagcgca gattttcggc     5520 cttacccgcc ggacgatcgt gaaaatcgcc gcagaagcat actacaggat caacaactta    5580
cgtcttactg ccgccgataa aaaggacatt ttgggcttcg attatgggtc aaaagagact    5640
ccacaatggc tgaaaaagtt cgttttttcg aagaaaatg actgtttgat cgataaatca     5700
tccggttctt acatttctaa gggcgctttt gacttcgcat acgcaaaact ctgcaaattc    5760
gaggatgaag tgttcaagcc aaccgtgttc gcgtccgtta cgcgtccgat cccgatcgtt    5820
tgcgacgcca tgtactaccc ggcgatgcac ggtgatatgg aagaatcgct ttggaagccg    5880 aaggagggt tttaggcccg gaattcttca ttgacgagtc cggcaagacg tggctcaact     5940
ctttcgaccc tgattccatt ccggagccag ccgccgagct ttcgccgtac gataaaaagg    6000
cggtggagat catcaaggac ttcttcgtcg tacttttccc gaatgacaag gaacgccgat    6060
acgttatgga ctggatggct tggattatcc agcacccgac aaaacgcatc aactactcgt    6120
tactgattcg cggcgcgcac ggttccggta atcgacgtt gggcgtgctc atgtcggcca     6180
tgttaggccg taaaaacgtg gctacgtgt caaacaccgt gatgaatggc cgtttcagcg     6240
attgggcgga aggcgacatc ctgaaaatcg tggaagaggt gtacgacaaa ggcgaccgat    6300
acagcgctat cgagcggcag aaagagtaca tcaccaacga ccgttttcag gtggagccga    6360
aaggccgcaa gccgaaggtt gtcgtgaata ccagcagcaa aatgatgttc accaaccact    6420
ttaacgcgtt gccacttgat gaaaaccagc gtcgttatct ggtggtgtcc acgcaggcgg    6480
aaaatcatct ggacatggag cgcgtatacg ggtcgaaagc ggaacgctcg cggttcttca    6540
agaacgtgta ccgggcgatc gaaaaccacg tcccggcgtt gaaagatgg tttctcgatt     6600 gggagatcag cccggagttt gaccacaaag gccacgcccc gcaggacacc gaagcattct    6660
caattatggc cgacgcttca acgacggcg tggaaggtgc ggtggtatca atgctgcgtg     6720
acggtacgac gccgggcgtc catcgtgaca tcatcttcgt accagcgttg cgagacgcct    6780
tcctcgaaac ggaagacgtt gaaatgccga aaacgtcacg cctcaaaaat atgcttatgg    6840
agatcgggtt taagccgggc ggcgtgctga aattcggtgg gaagtccggt cgtgtgtacg    6900
tccgaaagcg tgtaaaaggc gcatacgacg attccggaaa actaaactcg gagtgggcgc    6960
aaaaaacatt gaaaaagcac aatgcggagg tggaaaaact cgtcggaaaa gttatacctg    7020
acgaatggga agacgaggtt tgaccgatat aaaaaaggcc gggaaatccg gccttacaag    7080
atcacacggt atgatctcca tcaaccgctt tataccgcag tttatcttca tcatactcgc    7140
cgccaatctt agcaataaac acccctccaa cgtgcaataa acacgttatg agaaattcta    7200
tcgaagcact ttggtcgttc ggtgacagca tccgactaat atgggattga tgtgtgccaa    7260
cgtggtacgc aagttcgatt tgttttatct ttttagcctt catttcggat tgatatgct     7320 cttttagcct attttttaat gctaccctcg tcggcatggt tttaacgttg ctcatatttt    7380
aacctttcaa tgtaatttcg tagagaccgt tttatatcat attaggcata tctagagcaa    7440
acgatggata ggttacaaat ttacatttcc agcttgtaac cgccgaaagc cgcaccagtt    7500
```

```
ctggctttgt ccacttttg agtacaggtt acaagtcccg ttatccttat acatgggtaa    7560
tgttatgacc tataataatc atcgttttag tcactccgtc cttctaatta cccttatttt    7620
ttgtaacttg taacttatat gaaggaaaca gtagtaaaaa cagtaagata agagtcggtt    7680
acaagctgaa aatcttgtaa tccacttgta atctgtaact ccgacctgcc gctgccgtca    7740
tggtcagcac cagcccaccg ggtataaccg taatactatc aatcggttga ggggctaaag    7800
cgccgttctg cccgcaccac cgtcaccacc gcgatttgga gactccctac gggagaaatt    7860
cgattttct gctaagttat tgatttcgca aagcggggct gtggcagatc cggcccattt    7920
tccgagaaag cggctctgcg caccccgggg ctgaccgatc gccgggtaag taccttttg    7980
aaatcgtgac cgtaattctt cctcagccgc ccgccacgcc acgcaagata gatcgtaata    8040
ggtagtcata ccttcacacca cgatcgcccc gtctaccccc cgtagcggtc gaaataaggg    8100
catacaataa cgccccgtca caccatatag cagggatacc atagaaaggg gaatagatag    8160
ccatatgcag ccgcataaca acgcacgccg cgtatatcat gcagcaccat agcgggccgc    8220
catacggcat agcgcgcaca taaggccgct ttgatgcacg tcgtgtgtat caggaaggaa    8280
gaaagccgga cgggccgcca tacgcacgcc gcgtatatca tcgcacacgg cacaccatag    8340
gcccgctaca cggcaccgca acgcacgccg cgtatatcag aaaggcaata aaaaagccgc    8400
ccggataggc ggccttttgat acatggggaa tgtgtcaaaa caggttaaaa gggatcgtgc    8460
ggcgttcccc gaaaatccgg ttttagataa acgcttttaa cagcacgtta agcatcgcgt    8520
tagcgcgtac agtggcaacg gcaagacgtg cggccccgtc cattttgtac agcgtcacac    8580
ggaaagcgcg cgcccggtca tcccacgtta gatccgcatc agcccgggta aaagtcacgc    8640
catcaatatg acgcttaaaa ccttttgccc gtgcgatccc ggcataccga tccgccgcca    8700
tacgtgccgc cgttaagcgt tgcgccttat ccattgtggg ccgccttgcg gtcattgtac    8760
cgcgctaaaa gatcaagtga cgccgtttta cgcacattac agggaagccc ggcgcgggcg    8820
ctgtacgcca cgatcgccgc ccttgtcttt aactggtcat catgctggct tgctaacacg    8880
tccatgatcg gcgcggtgtc atcgtccagc catcgcaacg cgtagatccc gttatcacgt    8940
atcaggcgac gcgcggcgcg atattggcct ttattcatcg tttcccette taccgcctcg    9000
ccccggtcac aacgcgcgga atacaagcca atgcggcccg gataagccgc cacggcagcg    9060
cgacaatcgt cataagagat ccccgcgtca atcacataat catgacaatc cgccgcctta    9120
ttatcagcac caaccgcgcc gcacatcgtc acaacgaaaa accataagcc cgccataatt    9180
accaacctcg atccagttta atgatgttaa tacccattgt gatgatcctt atttgatgaa    9240
ttcgatggtt ttgatctgcg acgtcgtgac ggcttgcgcg taagtcttgt tttccagcaa    9300
atcaagacgc atcaaccacg cggagcaaaa caggccgcta tctgaaaaaa tcacgtcttc    9360
ggttttagcg atcaacgtca ttcccgcaac ggttttaatc ttgatgcggg tcgccgtctt    9420
gtcattgttg agcgtggcgg cccgtcgcg gcatacgtcg cgcgggcttg cttgatatat    9480
tgtttcatgc agccgacgcg caccacgtcg cggacgtgct caaccgtgtt tacgtcgcga    9540
tccagttcaa tgacggtatg aaatgcgcca tcaatgcagc aggacacgac aacgcgcaca    9600
cgataaagct gatattcagc cgggctaata cgtgtcgtga tttcgtaaaa ttcgccgtcg    9660
attttgtcgc gcaaggtatg cagcacgatc cccgatgcgt taacgtttcc acgctcaacg    9720
gcggcgcacg cgcgatcgac gtagtcggtc ggggctgtca cgtatcccgc tttaagttgt    9780
ttgatgaaat cgctttccgg gtcatctttg cgggcctgtt caaacggcac atattcgatc    9840
ggcgtgtcgt aaagactaac catgtgaata tccgggcgcg cgttcaggat ctccgcgtca    9900
```

```
tcaagatcta acatccagta accgcgcttt aaataaacgt attccccgc cggattggtt    9960
gagcgtaaaa cgtgatcaac cgcgtcggcg tcggcgttgg cgcttgccgc gtttaattct  10020
gcattcatcg cgatgatctc cgcttcgatt tcagcgcggg taaagtcgga aaggttgagg  10080
atgaaatcat cttcgaaccc gtgaacatcg aagaaaattg cgtcagtgcg caagcgttga  10140
gcgcgtgcgg cggcttcctg ttctgcgatt tcgtcggctg ttttcagtgt gccggaatga  10200
tcaagcgcgc tttctaacac gttttcaaag ttggattcat aagaccatgc acgccagatt  10260
aatgatccgc cgtccacctc gcggatctcg acttgcgtcg aaccgtattt atcaaagttg  10320
taagatacgg cgcgatcggc cttgatgtta tattttccaa ccattgcaac gatttgatca  10380
tgtgtcattt tgtatcacct gttttgctaa ccgtcggccc attgccccgg ccccgaaggg  10440
gatttaaata taaatgatat acgcggcgtg cgtcaataac ttttctcttt aatcgtcggc  10500
cgcgtcacct ttacggcccg tcatcccgtt ttataagtgc gtcgccttcg tcttgtgtag  10560
gccaaatcag gcgcacacat acgccccgg cgacggtata caaaaacact ttatacggcc  10620
cgacgttgtc gccgaaaata accgccgccc cgataaacgc cacgatcgcg ccgcacgcgg  10680
taaacttgat cgcggcctag cggcgttccc cgaaaatccg gttttattca tgatgtcacc  10740
tgtacgcggt aaacgcttat tacccgccag ccgtccacac attgcaccgc cagcgcggcc  10800
ccgtccgcct ttgagctttc cagtatcgc acatgacctt taacccttc gacctcatag    10860
actgacgcgt cggcgtccag atcgtacacg tcaccattaa ttacaatgaa ttgatccggc  10920
gtataggtga aataatcgcc cggcgtgcct tcaccgttgt gatatttggc ggcggcttgc  10980
gctttctggt catcggtcag atcttgccag tagaccgggc gcacatcgtc cgcgacaacc  11040
tcgccgacaa tatcccacgg cgatcgggat tgttcgcccg cgtaaaactt gccagacgcc  11100
gtccagatct taaactcgcg cggacggtat gcgccccggt acatttttcca gatccggccc  11160
ttaaccggga atgacacgac ggccccggcg ctattctcta aaacgatttg atccacggtg  11220
acgcggtcgc cgctacgatt aaagaaaagg cccggcgcgg taatattcag tttcatggtg  11280
atccccttat ttggttgagt ggttagcagg cccggcgatc catttcgacc cggcgcgatg  11340
tgctacgatt tcgacgctat agccgcaatt caggcggcgg cttacttcct tgtacccgtg  11400
gcgcgtggcg taattttccg cgcccttttc cgtggttgac gtgtcgcaat gcgtaccatt  11460
tgacaagata acgccatata tatgacccat agatcccccg attagttata aatagccgcg  11520
ttttcaaaaa attcaggcgt gtcaccgttt tccagatcat cccgtaaata ttcgtcgctt  11580
tcgcggaatt ccagatcttc gagcatatcc gaacaatacc cgtctatcgc ctcgcgtatc  11640
aattccgcga tcgtgcggtc atccggcttt ttcaggaagt cacggaaagg ctttaataat  11700
gattcgtcat agcatacgcc tgtatacggg caatcgtcgg acgcgttgaa caccccgcta  11760
acccatttaa cgaaagatgc cttttgttta aaaccgtggt tatttacttc acggtattca  11820
cgataaacgc ggcgacgcat attaaacgca ttaacattat taatgatcca cttgtacgca  11880
cgtacgccgg ataaatcttc cacatctgaa ctatgattaa cttcgtagcg aacatcgcaa  11940
cccctagac cgtatgacca gtcgcgcacc tcgacgcata gatcatcaca aaattcacgg    12000
aggctttctt tgtattctga aaagtcgaat tgatcgccgc tcttatattg gcggtaattt  12060
tcgatcgctt ttgctttcgc gacgtctgac agttcattaa aggtataaag tgaaatagta  12120
cgcatggtta cgcccttgt aacagaagag tgaaaaaatt atttgaacag ccgatcaaac    12180
ggcctgtttt acgtcgcgt aaataaaacg ttttgcgccc gaaagaataa cggcgctcaa    12240
```

```
ccttacagcg acgccatacc gcccgcgcgt cgtgatatat aacagccgca attattgaat    12300
aaccgatcaa gataatagcc attaacatga cgcgccccgg attaattaga tttcagtgtg    12360
aacaggcgat cgccgtcgta cagttgcaca tagtccgcaa ttttccagcc taaaagatcg    12420
cccctcgcg gcatatttca ttaatgcggt ctaacatgat tcccgccgca taacgtgcgt    12480
ttgcctgaat atctgacccg tcggcgacgc gcggcgaata gttaaccttg atcccgcgcg    12540
gcactaacca cgaataagcg cgcatgtatg ccgggcctgt atttgtcgcc gggcaaaact    12600
taacagtgat tgacatatga gcgggcgcga cttctggcac ataaccaata ataaacgtcc    12660
agccgttatc tttaccacgc acgcccggca cggatggcgc actattcacg atccccattc    12720
catcgagcgg cctttattca gtttaatgat tagcttttca gcggcggcgc ggtgattttg    12780
ctcactggat aacgccgcgt catattctga acgcgtccag ccattccacg acgtcgcaac    12840
gattttcccg ttatggtatt tggtgttaat ggtttgcata gtgatcccct tattaaatta    12900
gatgttacgt gtaaaatcag cggtgaaaat ttcgcgtcca tacttctgat aaatgacgcg    12960
taataaatca gcatcattca aaatatcggc gtcggtgaat tccttcccca tgaaaaagaa    13020
agcgtgctca cccggttaac gtggatcgtg ctgcgtagtt cgaccgtcgc gtctccgttt    13080
tcgtcgcgct tgatggcaat cgttaaccaa tgttgcaacg tctgacccttt gatcgcgtta    13140
tataccttt ccatcgtgac acctcataaa gttagtttat cgcctggact ttttgccccg    13200
tccccgaagg gaattcaaat gtagatgata tacgcggcgt gcgtcaaatc ttttttcgta    13260
ttatttgagt aaccgcacat aaaagcgcca ccgatcgcca cgccgggccg cattgcaccg    13320
ccgcgcccca cggcccccgc cggcacaccg ccaaacggca cgcggcgcca cgtcctaaac    13380
ccttgaattc tatatgaaaa accgacgcca accgggccaa aacaggccga tcggcgcata    13440
ggttaaacca ttgatttata acgatttgta cgaaattccg ccaaaaacga caaccgccca    13500
caacggcaga ccgcgccggg cctgactttc tctataaaaa ttcccgacgg cttacttga    13560
aaaagttacc cggttgaaaa attttgaaca acgcggccag tccttacttc aaaaacctac    13620
ccggctgacg gttttgtcca ccagcgtcgg ggcaatttca cccggccgac gggcttactt    13680
gaaaaacctg tccggttgtc gttgcgacgt tccgcgctta cttgaaaaag ttacccggtt    13740
gaagcccggc ggcccggcca cccgccttac ttcaaaaagt catccggctg aaactaaact    13800
ggagcgtcac ccggtcatca taattactgg atgaaatgaa ttgacatacg tcgcgtgtag    13860
aactattgtt ctccgaacgt aacatttaac gaaccaactg gagccatccc aatgagcaaa    13920
gaactaagcc cggccgaact gactggcgca atgatgacga ccgagccgga tgttgaactg    13980
ccgtcacgcg tgcgcgtgta cagcgtcgtg gggaacctca ttgcgctgga agtcggtggc    14040
gtgtacaccc tgtcccaaga actcccgctt gaccgtacgc tttcgcaggt acaggacgag    14100
gccaatgccc tcaaagcgaa gatgcgggcc agccttaatt cttccatccg gaacgccatg    14160
aaacaccacg gccaacggtt cagtatggaa tccgcactgg tgacttaccc gtctggccgc    14220
atgttcattc aggccgtcgt aacctgtacg gccaccgacg tcgcggacga cgacgaagtt    14280
taaaaacgta ggacggcacg cctgaaaaat ggcgtaccac ccttttgacc tgacacccta    14340
taggacgcac accgatgaaa acaacgcacc accctattga actgagtccg gtacgagaca    14400
ttgcccgtac ggcctttatc tataagaagc ccggccaaaa agagggcgag atctacatcg    14460
agaaggacaa cggtgacacc gagatcgcca cccctgacc cgcgcggacg ccatcgcatt    14520
gatcgccgga ctgcgtgccg ccttcgacct tccggacgag aacgccgaga aggtagaact    14580
gctacagcgc cgcctcgacc agacccaaga ccatatcgaa agcatttcgc tggtcactgc    14640
```

```
ggccaacatc atgttcgaga atggcctgcg caccgccgtg ctgacgccgt cccgtctgat   14700
caccgggcag atgcctgaac tggaaatcga cgcgactcgc ccggacacca tcacctaccg   14760
tctgaaagag gaaccgctca atgcagccga ctaataccgc gttgatggtg aacaacgcca   14820
tgcacccgaa aggccgcatc gacgtcgtcc cggcgttccg cgctatcgaa cggatctaca   14880
gcgtgaccat ccatgccacg cacaccggga tcaaggtgtc gtcggccacg aatcaccgcg   14940
tgaccttcta tcagtccggc gacccggcca tcgcgaagca cggcaaggca cgcggcgcgg   15000
acgaatgtgc ggccatgcgc atgtacatcg tgaagtttct ggattgggcc atgacgaata   15060
tgccatgccc ggaagtgcag aatgtcgtcg tggaggtggc tggtggaagg cattgaattc   15120
gttcgcgtgc agtaccaaga actgcgcaaa gtccggttag accaaatcac ctgcaaactg   15180
tctgcccttg agacgttttt caaggacatg aagacgacg tgcaggccca tagtaccaaa    15240
atgctcgacc tcgccacgct ggacaacgac gaggcggcgt ataacacggt cagcgaccag   15300
tacgctgaat caatggcggg ccttcgggcg gccaaagaag cactacgcgc cgcgatgttc   15360
catgcagcgc aatccatgta ccacggagca ccagccaatt taattaacgt aggagccata   15420
gagcatgaaa atcaagggtt atgagaaagc cattatcttg cacctcggcg cgctgtacga   15480
cgcggccaac gacggtaacg agaaggtcaa gccgctgcac cgcctgatcc tgaatctgcc   15540
gaacgttgac gaagaggcgg tgacgtcttt cgctaaagga gcgttaagcg atgcactcga   15600
aaagcatgaa gtgtcagatc cgccggaggc gtcttacaag acaatgggct tgcagcgta    15660
cggcgaagag gttgacagca aattcgccct cgccatcccg ggacaaacgc catcgtcttc   15720
cagatcgaga aacgcgaacg tgtgttgccc ggcgtcagcg tacgaaatga agtcgtgaag   15780
cgcatgcccg cgttgcggga gaaagagatc gagggttggg agccgaaccg caaggattgg   15840
gcgcagatga aggacgacgt ggaagcggaa atgctgaaat acgcgcctat ccgcccgtcc   15900
cgcgtcaacg tcatcctgtc cgccccgttc gtgtacgtgt tcacgtcgag cgcgaagacg   15960
gcagaagagt gcagcgcgct gatccgtacc gcgctcggca catggcccgt cgaacacctc   16020
ctgccgagcg agtatgagct gcgccagtta atgcagcgcg cggttctcgg ccagcaggac   16080
ggcatcaagg gcgatgcgtt tatccacctg aaacacgacg atggcgacga cgtcaagatg   16140
aaggacacgg acatcttcaa agacgagtcg gtggttgacc tgctgtcacg tcactggact   16200
gtccgcgcgc tggatctcga agtcgataca caatgcccgg gcatcgacac cgtgtacttc   16260
cgcctgtccg acaaagccat cctgtccggt atccacatcg gcgaggccga cgttgatgcg   16320
aactacgacg ccacgctcga acgctacggc accgacggcg gccagttcct gaccatgatg   16380
gctaacctgt tccaactcga taagtccctg cgtgcggtga tcagcgtgct ggacgaggcc   16440
gggcaggtag tcgagtacac cggaacgctg aacgacgaag aagacgacga cgaggtttaa   16500
caatggccgc gactaccgac aaaagcgtgc gtgaaactca cgaaaaactt ctgctcggga   16560
tgaaggacgg cgattcgttc tttatcgaag gcgtgaagcc gcaggatctt ggctatctgc   16620
gtcgaatggg ctatcggctt aacatccgcc tgtccatccg gttcacgttg caagaccaga   16680
tctacgggaa gatgggtacc cgcgtttacc gggacagagc ggacaaaaag gagtaacgaa   16740
atgggagcct atgccacgcc ccaagtagac caatactgga aggtcagaac gacaggccag   16800
atcatgctga tacgccagcc ggagaaccat gtgttcagtc cggaatggca cctgaactac   16860
cgccgggtac gcctgctgca tcacccgaa  tcctcctgcg tctttgtcga ggactacggc   16920
acctgcctga gcgcgctgga tgacccatgc gtcatcgaac tggacttgaa ggagtacaaa   16980
```

```
tactggaatc ttatttacag taacccgaca tatgattaac tgcggactcg gcatagtgct   17040
tccttatcgg ctcctgcgtt gtccgcttta agccagtggt aatcttcgga tgccaccttc   17100
caaaagcccg caatcccttt acgcgggctt tcttttgccc cgaataaagt tattgacgta   17160
cgtcgcgtgt acgactaata ttcccgtacc ataacaaagg agtcatgccg atgaagaccc   17220
acgtaatgaa attcgtacct ttcaaccaag cgttgatcgg gaaagaagtg ctgtacgttt   17280
tcccctgcca tacgggccgc gctgcctgat ccgcaccaac ggaacagaca ttgaagtcgt   17340
taacgccgac accactgaaa acctgacggg attcgtcccg gatctcgaag accacgtacg   17400
ccgcctgtac tcggccatgt tcagcgagcc taacccgaaa tacacgcgga acggcgaaca   17460
ggtcgtgttc ccgttcatgg tgttcgacgt catcctgcat gaccgttcat ccaccagcaa   17520
cgacgacggc agcgctgacg gcgtcagggc ggcgctggaa gattgggatg acattggcgt   17580
acccatgaac gccgaaacgg ccgccatgac gatcctgtgc gccatgctgg acgaagaatt   17640
catcgccggg aagacggttc acgatttatg gtggcaacgt gcatggatta aacgtgggct   17700
ggtgtcctgc ggtctggcta atccgtacgt ctacccccgc ccccgctgaa atggctgacg   17760
cagtcgcctc gcgattgggc ttgggagagc ggcggtatcg cgtcagacct gccatccgag   17820
aattgggaca tgatctacaa cgtgtttcgc cggaagttcc gcgccgcgct tctggccgat   17880
gtatggcagg gctggaaagt cggccggtggt gcattccgca ttttgaaaga gaggacgtt   17940
gagatatgag aatcgaagcc aatggtggaa gtcatttatc cgtcgtgcag catagcgacc   18000
agttttattg tcgcgactgc cagaagacat gggacgcgaa tgacatcgac ccgccgccat   18060
gtaccgcgcc ggagtcagac gagccgaaga aaacgatctg gaaacgctgg caaggcggcc   18120
cggcctgtct ccagaacctt ccgaaagacg agccgaaagc aactgttacg accacgccca   18180
ccggacgtcg cgtttcggcc agccggctt tcgcctatcc gtacggcacc ccgcgtccgg   18240
agaacgtcga gcggtaccgc cagtgccgcc ggagtggatc gccgaataca tgagcggcgt   18300
cgataaggtc gtgcagaccg tcggcgcgta cgtgctgtac acggacaacg cagccacgat   18360
ggtctacgcg ctcgacgcat tgcaggcgat ggaattttc atcaatacga tgggtaactg   18420
gatgacggcc agccagatgt acagcatcag cgttgaccgc atgagcagca tggatcaata   18480
cggcaccggg cgcacgccgc gcgttgaaat gaatcctcgc gtgatggagt cggccagcct   18540
cgccagatcg aacagcggcc gccagcacaa aatcgttaac atcgttgaat tctctaacat   18600
cttaaaggca tccaaatgag cgaaccaaaa gtcacttaca tcaccgacga caaaagcctg   18660
aaagacatcc tcgtcatggc tatcgagcag gaaggcggca tatccccaaa tcatatcctg   18720
tgcgtggcgc ataaatacct tctcgataac tgcggcgttc cggaagggaa catccagtca   18780
gtcgatgaag tcgaggtgga cggcgacgca atgccccggg aaatccgcat tcactggacg   18840
cgagttaaac gcccatcggc ggttacgcca acggccgcag aagtgaccga gtgggagcgc   18900
gagcagtgcc agcagatcct gagcaccatc ctcgaaacgg tacgtgccag cgctaaatac   18960
gcgaagattg caggcaccac cagcatcggt ctggccggaa gcctcgccat gcaggacata   19020
cagcgcctta ccggacagat gaccagcgat ggcccgctga cgctgaaaga cttcgaaccg   19080
ctgcgcctcg ccaacatcac gccgggcgaa ctggccgcac tacgcgaagc gctggatacc   19140
aagacccgca gtctcgatac ggcggaaagc gctgtcacca gcctgcaaat ccagttagcc   19200
gaggcccacc gccgacacgc tgacgataac accgagcacg acaggagat cacaaagctg   19260
cgcgccacgg ttaagtcgct acagaataac gtacggtaca cccgacagtc cgcgtccgtc   19320
cgtgccgcgt gggaagaact ggcggccatc gaccttacgg ccgctcgcat ggttgtcctg   19380
```

```
tccgccttcc acacataccc gttacaggcg gcggaatacc tcgaaatccc gcactatcgc    19440
attgatgcag atctggtagt cgggcttcca ccgcaagtaa cgtcgttcat ccatgcgatg    19500
tgcgataacc tgctgctgtc accaccaccg aagacagtca cgcagcaaat ggtcaaagac    19560
atgatcaacc gcctccactc cctcgcgagc gcgtccacgt tcagcgatct gacccgcaaa    19620
tatgcaggcg tccattcgct gacaatgatg tcggaggaca aatacgaagc cttctaccgc    19680
gaggccgaag acctgcttaa cggagacacg ttttaatgag ccagtatgtt gatgcactca    19740
acgccatgaa aaacatggac gaacacgaac caaagatgat cggcgaccaa tggcgtacgc    19800
cggaatggct gtttcaagcg attaacaagc tgtacgggcc tattgtgctt gacctgttca    19860
ccgacggcca gaacgccaaa tgccagcgat tcttcacggc cgaagataac gcgctgcggc    19920
aggattgggc gaaacgtctg gcggaaattc aggtggagaa cctcggcctt ccggctttg    19980 atgacccgta tcggattcag ggttgggcgt atgctaaccc gccgtacagc cagaagcgcg    20040
ccgggaaaga acaccttacc gggatgaccc acatcatgcg caaggccgat gaagaacggg    20100
ccaaaggcgc tggcaccatc tggctgacca gtccgcgac atcggaaagc tggtggccgg     20160
acgccatcgc tactcgcacc atcttcatca aggcgcat cgggtttgaa ccgccagtct      20220
ggttccggcc gaaggaaggc agcagcgaaa tcacgtcggc cgggttcggc gcggccatcc    20280
acatcttcga cccggcgact gaccgcattc accccaacga gtatatcgac cgtgaaacgc    20340
tactggaaat cggcgcacca ctggctaacg tatcggccaa gatccggaac cgctggatca    20400
agatgtggga cgagatttaa agaaagcgtt tgacatacgc gacatgtgta attaatatta    20460
ctcccgaagg ttaatccacc aacgggagtt ttttattatg gtagacgtga agaaagaacg    20520
cggtctgaga aagaccagca gcgagaagtt tgaagaagcc atcctcaacg cgctgaacat    20580
ggacagtttt gactacgagg acgacggcga tatgcgcgac cacgcagtga agattatcaa    20640
tgacctgcaa tcctcgccga aaagcaagga tcagtacgac gccgaggatt tccgcaaggc    20700
cgtgctggcg cagttagggt tagaccaagc cggatacgcc acgccattga tcatgaagga    20760
acacgttctt ggcctgattc agtcgctgct cgataccgaa cagaaatacc tgaaactgcc    20820
gaaaggcaag acagacccga ctgtcacggt attccatctg gagcggccag ctttgagcca    20880
acccacggcg gaaatctgcg aacaggtctt cggatacatg ctggatcgtc tgattcagtt    20940
cgagcgcaaa acccgggac tggaattggg atggatgcag ccggactggc cgaagcaatg     21000
ttccgacgcc atccgccgct gtcttgaaga gaatcagtac atagacgcga tgaattacat    21060
catgttcgcc ttcgcgcagg gatggccgct tgatgaagcc ctcgtcacgc cgaaagccgt    21120
tgcaccgtcg gccgcccggt catggcagta cgaattccgg aacgtcaaag acagcaacga    21180
ttattccgaa ttagtcaaag tgctacatga tgcgctgaca caagccgcgt atggtaaagg    21240
gcgggagcga cacgccaatg acctgccgtt cagccagcag ccgatgaacg ccatttctga    21300
cctgatcgat agcccgcttg gattggtcta tcaggtgtgc aagaaggtcg tagagggcgt    21360
caacctgcca acgcatgacc aaagggttag ggagttgctc ggcgtgatca attatactgc    21420
cgggattgtc atctggctaa atcgccacca atcaaatcca ccgaaggaat aaaggggcca    21480
ccatgaagaa gatcgctgcg ctaacgctgt ttgtattgat tatctgcggt gtgctgtttg    21540
tcattggccg tgtgggcgcg gcgatcgggt gtaacgacgt cagcgtccag accgaactac    21600
caaccaaata cagcccgtta agcggctgct acatcaaacg agacggccaa tgggagccgt    21660
tagactggag actatgacca tgaaaattcc cgcaggagac gttaagccgg gtgtactcgc    21720
```

```
gaccatattt ggcgagcagt tccgccttcg ctatatcacg tatcacaacg ttggcagcgt   21780
cacactgcgc ttccagccgg gcgacgaacc gctgtcaccg ttcaccgaga atgacgtgct   21840
gaccatgacc gttccgcgca cgttcgaagt cgaggtggac accgatggcc gatgaagagt   21900
taaaacttaa agtcggccgc acctatcgcg gtaaacggcc gcagaaccga acggactgg    21960 tgaacgaccg caccatcctg tacatcgggg ccacgcacat ccagtacgac ggcccggtcg   22020
taggcttcgg ccgacactac ccgagttgta cccgcgaagc gttcctgaaa tgggccgagc   22080
gcgacgtgac tgacgaatta ccgaagggag aatacgcaga atggccgata aaaattgag    22140 attcggacac ctcgaaactg gcgacatgac actggagcgt aacagcatcc gtatcgggta   22200
cagcccggaa gtaaccttcg ccgtgaaacg acgcgtagag cgcaccacgc cgacgcaggt   22260
catcgtaggg aatacgcgct accggaagga cgatggccgc gccattggcg aagccgggtg   22320
cctgtttacc gaggacgaca tcggtgaagg gaaaacggtc aatatcgaga tcgtaaccga   22380
ggccgaattc cggagagatcc aaagcctgtt ctacgaattc aaggccggag ttttggccgc   22440
gtgcgaaggg tatgacatca ccgcgaatga cttggccgtc ctgttccgcg aacgggaagt   22500
gcgcgaaggg atagtggcgc gctggtggaa aacgaaggaa acgatcgcca acctgcacaa   22560
acagacccgc gatttcatgg tcgagaaggg ccacggtgat cgactggagc acgcccgaa    22620 aagaaagtct tagaaactgt ttgacatacg tcgcgtgtat aacctatatt atcccgaagg   22680
caacaacggg gattttact ttaggggcaa catgctgact atcaccgccg aagaaatgta    22740
tcaagccgca actgaccacc acactgccga agcgattgaa gtgcgtggcg aggtggagca   22800
tcttatccgc cgggccgcat cggccgggct gacaaccact acggtcgcgc tgttacacaa   22860
cgaccacccg ctgtccgata aatcccgcgc catgctgatc ggctggataa aggacgccgg   22920
gttcgaaatc tattccgatc ctgacagagcc gccatgcaca ttgcaaatct tatgggggag   22980
ggccgccgca tgaactacat gcgcatgaaa gccgaccgca cccacgccgt catcgcagat   23040
ctggaagcaa aaggctatct ggtggccgtc aacggtgtcc acgacgagat ctggtttgac   23100
atcatccatc aggttgggcc gatgtccgca gcggaacgcc agtccattga agaccgactt   23160
ctggccgcat acagcgaaga cttgaaggag tgggctgacc acctgctcgg atcgtggcgc   23220
gaggcgcacc cgggcatcgt acgcatttgg gacggcgtgc ctgtccgtaa tttcaacgaa   23280
gaggataaat ataaaaaatg aaacgcggat cattattcca gcaggaggcc cgccgacagg   23340
cttcggtcat ccgccaacgc gcgaagtggg atctgtaccc gttcgtccgg catatcgtta   23400
agcgactcct gcgcggcgac gaagaagtca tacgctcgat gtacgggaaa gggctgcccg   23460
acgttatggc atcgttctac ggtataacac gttcgcccgg gccacgccgt atccacgccc   23520
ggtctggccg tccgtacccg ctgctgttca tcgtgcgcga aggctcgccg atacacatgg   23580
atccggtata ccgccagttg actatcgatc cgtggctttc gccgagggac gcgctggccg   23640
cgaagggaat caagatagaa aactcggacg acatcatcca tctgctgtcc gtaaacgatt   23700
ttaagtacgg gctgcggttt accattaatc ctgaactggc cgaggactga catggctacg   23760
atgaaagagc atcacaagat accgcacttc cagtacagcg gcggggtctg gtactgctac   23820
cgggcgtttg acgcggcgc aaagtcttac ccaacatact cgcccaccag ccacgccgag   23880
ttgtggtact gcgacaaggc gatggcccgc atggtggagg tgtacggctg gtggaaagcc   23940
aaagacccga agaatgcccg cctgaccgat gccatgctgc tgcgctacgc cgggccattc   24000
gctacgtgga agaaggtagc cgacggaaat ggggcatggt catcaaagac cagcgcatct   24060
tcgcggagaa cgtcggtagc cgcttctcgc gggagtattt cgcccgggca aggaaagagg   24120
```

```
atgtcaagcg cgcgaaaacg atgcgcggca aggaacaggc ccggctggcg gaaacgctga    24180
tagcctcggg gtactgccgg gtgtcgaata accatcgcat cgtcagccgc atcgatcgtc    24240
ctgactggcg agaagtgctg gcgctggaac tttgcccgca agatccgtac ggtgccggga    24300
ttgaccgttc gtacgggagc ggcatggccg acttctatcg tcgcgggaac agcaaggata    24360
aactgaccat tgaagacgaa atggtcttcc ggcgcttccc ggttcaggcg acggcccgaa    24420
ggacttcata ccattatgcg aggactcaac cgatgccaac taacaaagcg ccgcttgtcg    24480
tcagcttttc cggcggccag tccgaccttt ttgacgaaga ctttgaggag gatgaagtat    24540
gatcgacgtt gaggctataa aacgaaaata ccgtgccaag ataaaaccgg gctggccgat    24600
taaaggcgac tccgtgcatt tcactgaccg attcaacggg cataaatact acggaaccgt    24660
gctcgaatgg gaacgcaccg ggccgcgtga agaggatatt ttttggcggg tgcgcctgcc    24720
tagtggggat attatttcct gcgagttcag cgagattaat caggtagacc gatctcctga    24780
aaatgaaaaa tacgtggacg aatataaccg aggcttaata tgaacgtgaa tatgtgtaac    24840
ccggcggcca agcccgtcat gatctatctg gccgggccgt accgcccgta catcatcggt    24900
tcgggctgca ccgttccgac gacggtcaac atcctgaaag ccgaagagac ggccgtgtcg    24960
gttgtcgatc aactttacgt ccacaagatg ttcccggtta ctccgcacct gaacacggcc    25020
cacttcgagc acaagacaga gggcgagata ccggacgaat attggctgga atgcacgatg    25080
gaattgatgc gccgttgtga cgcggttctg ctgattggcg aagatgcgat gcgcagttcc    25140
ggtacccgcg ctgaggtgga agaggcgaag cggctgaata tcccggtctt caataacctc    25200
gatcatctgg tgtcctcact gcggtaccac cagacaatcg agggtgaacg tactgtgatt    25260
attacccacc cgaccattta actatttcca gccgcatagc cgttcgccga tttcatcgtg    25320
ggtggcgatc tgccgtgcgg tttcatctgt cagcacgtct tcctcgccga tgtagatggc    25380
gcgcgcgaca gaacagaaag acggcgcagg gttaatcctt tcgacgcatc cacttacggc    25440
gaagcagatc gttagcgcca ccatcaggga gtttattgat ttcattatgc acctcggcca    25500
catttttatc cgcgttttgcc tgttcccgca acgtgtcgta gttctggtta ttaatctgat    25560
cctgtttgcc cttcgcgcgt cctgcccgcc agacgccgaa gagggccaca acgaaaacga    25620
gcgccgcaag gacgcccgtc ttaatccggg cgagtagccc cgtcatgcag cggccccggc    25680
ccgatgcttc cggtacgcga cccatcccat gtacaggcca atcgcgattg tggccgcgcc    25740
gaatgcgatg cgtacccaat caccggaaga aatatcgccg tgggcgctgt ccatcgcagc    25800
cttgacgggc tgtaccatgt caaccagttg cgccgcgccg agtcctgcca cgcttgtcgc    25860
agccacggtg gtacggttaa caggcttggc cgccttaacg atgcccgccc ggcgcagacc    25920
ctcctcgatc acttcgtccg agtaccacat attcgcgttg ctgtacggcg tcaggccgaa    25980
cgcttccggg ttcccgtttt cgtggcggat gatgccttcc accagaccgc gcatggtgtc    26040
gtagtcgtgg agattcagcg tttcgctatt cgggtcaacg gccagaacgg cggccacctg    26100
tttagcgtat gcagatacgt tgttctcaac ggcgggtgcc caccgctcga tcacttcgcg    26160
aaccgagtcg attttgctgc cgtcgttggc cttgcgcttg tcgtagtagg tggtcagggt    26220
gacagcaatg gcgcggatgc cggatgccgg gtctttgaac tgcgcgaagc ggctgtccgt    26280
cgcctcgtta cgcgggatca gaccttgcca cggcgacccc cactcgatgt tgcccgggtt    26340
gttattgcga atcccgcgcg gcttctgttt agccatcggt tatttcctca tcatttggga    26400
agatagggta tccacgcttt gtttcaggtc gcgcatgtcg gcgcgaaggt ctgaacgaag    26460
```

```
ggcggagttt tgcgagacgg tttcggcccg gagaaccgtg aacgccgctt cagtggagtc    26520
ctgacgtttc tctacgttgg taagccgggt gtccgtctgc gtgttctgat ttgataggtc    26580
ggcgaagcgg ttattgacgt acagtaccgc cgccaccagc atcgaagcca tcgtcagaat    26640
cgtggggaga ttgacagaca agtctaactt gatgccgccg gaggtatccc cggccgttcc    26700
cgttccattt cgctcattgg gtgcttcctc acaaaaaaaa ttagcgggac aagcccgcta    26760
agaatattaa cccgtcaatt gtcagtacac aaagcggcaa gtgatttgca cccgatgttt    26820
ccgtggtggc tgcggcattt cgtacatcga cttgtcgcgc atcattacct gctcaagtac    26880
ctgacggact cgtagcgtgg attggggagc atctttgtct gggtaattag ctttatcggc    26940
atagtgctgc aaaacttgag acaccgttgc aaatgattgc gggacgtcct tgtcagggta    27000
ttccgccgtc attgatacat gctgaattac ctgccgaacc gcaagcggtt tatgcagtgt    27060
gctccaatcc gggtaagacg catcctgtgc cgcctgctga atgatctggc tgacaataag    27120
cggccggaac atggtaccgg gatcagggaa atcgtcaatc tgcgcaacgt gttccaatac    27180
ctgatttaca atcgcgtccg acgtcggcag gtgggcgtcc gggtagtcgg ccggggtcgc    27240
gatgtgctcc agcacctgat tgaccgtcag gtaggatacc gggacagtcg ggtcagggta    27300
cgtcgcgcgg aacgccactg gctgcattac ctgacgaaca tggataccgg actcggcaac    27360
ttcacccgga ggcggcatgt attggtaccg cgtcaccagt tcaacaaatt gcgccagcgg    27420
agcgtacgag atcgggagcc ggagcggttg ggctttcacc accttctcta ataactgcgg    27480
cacggtctga accttgctcg cctcccacat gtcgttcggg tcttcgtagt ccagcgcttt    27540
catgacgtgg tacgccgtgg ccgcactgac gatggccgac gttgtaggga ttcccgggtc    27600
agggtagtcc gttgcctgct gcaccaccga catgcgaaca gcgtcagcgc gcgaccatac    27660
cagcaggttg atcggaggcg tgtactcttc cgcccgcacc gcatagccgc gtacctgttt    27720
aacgcgcgtc cgagacagca ccgggcgcaa gtcagacttg accaagaact gagacgaaac    27780
gtgtttggtg cgcatccgag acagcaccgg gcgcaagtca gacttgacca agaactgaga    27840
cgaaacgtgt ttggtgcgca tcgtggacag cgggatggtt cgttggttat cgctaaattg    27900
cagcaccagc ggcgtcaggg tcttcgcgcg cgtgtaactg ataggaagcg cacctgata    27960
ctcgcaaaca gcatacgacg tcactgcggc cgcgtgctcg acaccgacag tcgggtcaac    28020
gaagtccgcc gggatgaccg cctgtgcaag cgtctgcgcg cgaacacgt ttgaccgggc     28080
atcgggatcg gcaacgcggt aacggcctgc gataatgcct gcgccacgcg agtccttgag    28140
cgcgggagtc gttcaaccgg gcgcttctgc gcggccagaa ccacgttcga cttcacggac    28200
gcaggcgtcg tgtacatcgg cagcggatgg gcctgaacca ccagcgtcga ttcatggcga    28260
acgaacacac cagacgtcgg gacgtacggg atgtcgatcg actgcaatac cagattccac    28320
gcctgtttcg tgctgatctt cgaccacatt tcatccggca gcgggaagtc accgagcgtc    28380
gcggacacca cggcatacga ccacgcggtc ttcaccttgt cgtacgaaat agtcacgata    28440
ggcgacgcca gaacggacag cgtcaccgcc tgcttcacga tgttgtagga aatcggggca    28500
tcgatcggcc gctggacaat ggcgtaattc cacagcgagt acaggcgttc cgtcgaaatg    28560
acatccgaca acgcggtac gacatcgtgc tgcgtgacga actgataaac cgcgtccgcg     28620
tacagcggcg gccgttcagt agccgcctga ccgatagcct cgcagatcat ttcggccgcc    28680
ataaattgcg gctctttgac cagcgcttca cagaccatcg ttgacgcgcg gatctccatc    28740
ttctgaatcg ccagcacttc gccgaccaat tcggccgcgc ggaagacggt tggcaattta    28800
ccgtcccact gcaaaacctc cccgaagttt ttcgccgcgt ccatgttcaa tgcggaaatg    28860
```

```
gctaacgctt cgccacacac cgggacaggt atgtgagttt gggcttctcg ccattccact    28920
gcaaggcttc gccgaccagt ttggccgcgc tgatacctac gtcttcatcc gccacatggc    28980
ccccttacgc gacgaatttg gtaccgactt taagcccggc cagttttgta aggttccagc    29040
gcgagccatc cgccgggtca gacaccatct gcaacgtgtt gaaacgccac aggccgcctt    29100
gttcgagcgt cgatgtgttc tcgctttggg tttgagtggc cccggacttg gcgatcgcgg    29160
cagattgtct atttccaagc aacggatttc gggccatcgt ccggacgtta accgcttcaa    29220
tcgacgccag acgtgtgctg actttggaaa tgtcaatgtt atacaggtct gctgtccga     29280 ccacgtccgc ccgagaattg cagtagattg cgacggcgtc ggggtgatac ccccggcaga    29340
gatcggcgtt accgcgacgg cggcgtttga cgaatatgcg tctggccgag agaactgtac    29400
aacatcgtca ttaacgggat tgaacgcata tactttcgtc gaagacccga ggcgttgatc    29460
tgcatctgaa acgattttct ggacatacat gtcccgcagt tcaaaaccga gaacggtgt     29520 ggagctagtg gtagagccaa cgtaatgttc gcacatcaaa ataaggccgt acgacatatc    29580
gtaggcggtg tagttggtgc gggtcgagac aatttcgtcg ttcagataga tgttaagggt    29640
cttggtatcc gccaaccatt ccacctccat atacttctcg tcctgaccgc aacgatcgga    29700
atacgataca agtctcggcc ttctgcgctg ctaatacccg ccgggcagat atagacttga    29760
taaccaatat tgtatgtggg gtgtgttgcg cggccaatac ggaagcccat gcgccacgac    29820
gtcgtcaggc gttccgccga aggccagcac aaatcaattc ggaactgcca cccggcccac    29880
cagtcagatt ggttagacgg ttggtattgt tcggtgctta ggcatggcac ggagttatca    29940
aagaaagacg gcttaacacg accaaaagca taagacgacc cgtacccggc agacggcgac    30000 catttcatc cgtagtaagt gatcagaggg agaaggccgc cgttttggtt gccgtttccg      30060
cctcgaccaa aaacgttatt aattaaattg tcggaggaga gggcatggcc tcccgccacg    30120
gtatcgtttg tgttgataaa caggttcgac tgaccctgac tcatcgtgtt attgatgatc    30180
ccattaaaac cgcagtgcca aactacaggc atagtgaatc cctcccttat cgagtgatga    30240
tgccgaattg caaagattcg acgttgttct ggttccagtc acttccgccc ggcgcttgct    30300
cgaacgatgc ctgataatac ttatacgact cggtaagcgg cacctgaatt tcagtcggcg    30360
taccgccttc cgtgttgacc accagaccga gtttacggtc atcaaggtcg cctttacggg    30420
cgtacgcgat aacagatacg gcgaagatct ggttattgtt cggcagcgtc acgttcgaac    30480
ggtacatatc ggtcgcccct gcggtgttcg attgcaggta tggcttcgac tcgccgcccg    30540
gggaaagctg tgacacgatc tgatagtgcg gcgtggcaga cgaggcgttc acgacttccc    30600
actgcgtaga aacgtcggcc gttggcatac gactggtcac ttcgaccgga gtcaggcgcg    30660
cgttgttgcg gctaccggaa ccgtcgatca cgtagaagtc atccagtgtc tgttcgccag    30720
cattaggtgc ggtacccgtc tgccccaaac gattgtgtac gtggtggtcg gcgcactcga    30780
tggcgtaacg gttaactgca attcgttatt cgcgtagacc ttgacggtgt tggccgtctt    30840
atcgatctcg atttcaaagt aataccatgc gttcaggatc agcgggttga cgcctaactg    30900
ctcgcctacg cggatttttcc cggtcgtggt gtcccactcg atgtccacga tgttctcgat    30960
acgcgcgata cgcatacggg atagcccggc tttcatggca aatccgaaga cgactgacga    31020
ggccgtcgtg gtgaatcccc atgacagtga ggcgttgaca gatgaactgg cggccacggt    31080
gaatttcagc gcacgcgcac ctgtccggcg ccctcgaca acggaaaacg tggaatcgct     31140
ggcattacgc accacgtacc cggcggcttc cagataactt tgtagggccg tacccttcgc    31200
```

```
gccgatttcg gcatagtggt cgtacccgtc acagaattta acatttcggg tatgctcctt   31260
atggtcttac gatgacgccg aacggcgctt cgctgagtcg ttcgtcattc cagtcttgcc   31320
cggccgcgtt cgtctcgaac acagcataac tatactttc agtcgtggat agcgccgcgt    31380
cgataacttc ttttttgcgtg tcgccttttt ggccgatgac catgcctaac tgacggttgt  31440
ccacgtctga cttttttgttc agcacggtca tgccgacggc cagaatgttt tgcgtatcag  31500
ggatgacggt gtttgataga aacgtgtcgg tcgcgccgga cgtgttcgac tggatgtacg   31560
acccttcgac gggcggctga ttgtagacga gcgggtagtg atcattgccg gatgacggcg   31620
accattcttt gtccacgtcc accatcggca agcggctggt gatctggata ggcccgatgc   31680
gcccggtata cttacccggc tggttgtcga tgaactggat gtcgtcgaga aggtactgcg   31740
ccgtggcaac gcccgcccat gtgacttcat agttagtgac cggttagcg ctcgacggcg    31800
atggcgcggt gatgtccagc ccgttgttca cgtacacctc gatcgtgctg gtagtcttgt   31860
ccagaaccac ttcgatgtag taccacaagt ccagcagcag caccgctgtt ccggtaccgc   31920
cagcggctgt gatcttcccg ttagtctcgt cccatgtaac cgtcgccacg tccttgatgg   31980
tgatcagggt gtggcgcaga ccgatagcgc ggaaggcaaa gccaaacacg actttcgtgg   32040
cccccggaggt aaacacgcgt tcaggctgg ccgtgtccgg cagtgatacc gccatctgcg   32100
tagccacgcg tccttcttct aacgtaggcg tgccagacac ggtgtacccg catttggtca   32160
gcccatccgt aacgtcagac cagccgcgta gctggtcaaa accgtccata aatttcagca   32220
tagtaaccc tttaaattac tgaacgcaca ccgaattcgg cggcttcaat ggcggctcga    32280
tcataaccgc ttgtggtgaa ttgcgcgtaa cgatattccc aattacggcc gatattcgac   32340
agggtaacgg tgtgactgtc aatgttcgcg ataatcgaca ccgggtcggc cgtggccttc   32400
cggactaatg cgatcagtcc ctgcgccaga atggcccgtt atccggtaac ttcgccgtcg   32460
agataaacga gtcgtgacgg tcattcgtac cagtgtagat gtacatgttt gccatgtctg   32520
gcggcagtcg gccgaccatc tggttatgcg ctgccgtcgg gttaggcccg gccacgcccc   32580
attcggtatc acggtcgccg tccggcagac gtccgctgat ctggatggcc cctaagcggc   32640
cgccgtcctg cgcgtacatg tcgtcgaata ccttcgtgtc ttccttgtag ttcgcatcgg   32700
cagggaacga tggcagcatg tcgaacgggt tgaagaccat gcgcacgacg gccgacgccg   32760
caatgacgtc cggcagtgta taggctacgt ccgatttccc gttgacaaac acctcgataa   32820
ccttcgtggc gcggttcatc acgacttcat agtaatacca gcgtgtcggg atcggcgtga   32880
catacccgac ttccgactgg tctggcccgg tctggatggt gacgagcgcc gacaccgggt   32940
cagtgtagac aacgacatgc ggaacatcgc ggccagtggc gtcaccgacc tttagcccaa   33000
atagcgcgcc acgctcctgc tgcttgcacg caaagccgat ggtgagggtg tcgccacccc   33060
atgtccagtc gcgctcgtag gcgctgttca gcgtgtacag tccgatgctc gccgggaggc   33120
ggccaagacc cgccgaaatc gcgcctcgaa ccgtgtaccc ggcgagccgc ataaaggttc   33180
ccggggttaga cgtgtccgtc gaacggaact gctcatatcc atcaaaataa cttgccatgt   33240
gatcccttag accagtccca tgcgaattac gaagccaaag ttttcatcc cggcgacggc    33300
ttcctgctgc gcgcgaaccg tcatgcgatc cccggcggcg aaggaaatcg ggttgccccc   33360
ggcagtggta aacgatgcgt tgaagtttcc gatttccacg gtcatcgttg cgacgttctg   33420
gccgttgcgc tgcacgcgga attggtaata ggccgggctt gcgccgtcgg ccatgtcgaa   33480
ctgtgagcca accatattgg cgggcagata catcgggtca aggatcggca gatgcacgac   33540
gggttcattc gcgtacatgc tgtccgacac tgtcacgccg atgtcgtacc atttcggctt   33600
```

```
aacgcttggg tcggggtcag ggttgaccgg gtctccccgg tcgcctcgtc aagccacgtc    33660
gtgccgttaa accacaagaa tttctcgtac gaacggacgc gagcgcgcca tccgtaacga    33720
ggcttgtaaa acgtccagac cttttccacg tacacggcca catcgccttc atgtccgccc    33780 acgcccgtc  gggttagccg cgacgacgta ggtggcccgt ccaccacgtc cggcggcgga    33840
gcggagaagg tcagcgattc cagtgtcagg aatagcgtgg tgtcgaggaa gatttgcgag    33900
tcggacatcg ggccacccaa tagtcttccc gcgaatccac ccgtagggta gccctgatt     33960 cggggctgtc ttttcggca  ttattcaggt tcctcgtctg ctggtggaac atatcggaaa    34020
tctggcagtg tcatcgccca accgtgatcc caactcaatg accatcccgg tacgttggtc    34080
gggtcaactg gcggttccgg cggttccggc gggtcagtat ccgggtcttc cggatcgact    34140
ggtggctgcg gttcttccgg ctcgtccggc ttcgtcggct cggatgggtc agtggtgccc    34200
ggctcgctcg ggtctggacg atccggcggc tccgtcggcg gagtagtacc gccagtattg    34260
ccaccgcccg gcgggttcca cggcccatcg ccaccgcccg gtttctgtcc cggagggagc    34320
gggaaggacg gcacgcgcac ggtcatcgta tatccctgcc agttcagcat tccatcacga    34380
atcgcgttga cggtcacgtt taacgtggaa tagccaccag cgtcctgcgc atagcccgcc    34440
tgacggcccc aacgttcgag gtcggcggca cgcataatga agcccgcgtc ttccgtttcg    34500
aactgagaca gcagcgagaa gccgctaccg gactgcgacc agtacgcata accaatgcgc    34560
acgcggtact tcacgcccgg ttccggagtg atgccgacgg cgaaatggtc gcgcgccgtg    34620
tttgcctgag ttacgcggtt gcggtgggcg tacgtgcagg ccacgtcttt cgctttcaga    34680
ttgttgtacg ggttgaaatc gtctgccagt ccgctcgcgg tgttgaagaa cggttggccg    34740
ccaatcatca tcagacccgg cgggtatgga cgtttcggac ggtactgcat ctgcaactgg    34800
agcgggtaca gcttgttcag cgggatgtcg gtgccgtagg tatccgggcg aatgatgacc    34860
atcgcctttt cgttatcgcc gaatgccatg tcggagtagc cgaagcccac ggagatcagc    34920
cagaccggac gtttgctgta gtgctgcgcc ggaatggtat cggccacgcc acgcccgact    34980
ttaaacgtgc ggccgttgac ggcagtgatg gacatcaatt cctgatcgat aagcagcaga    35040
tcacccacct gcgcgcccgc aataggaacg ccgtctttat ccgacgtcgg gtcaatcgtc    35100
acttcgtcag tgaagaagcc gaggccgacg gtggtcatgc cccacggtgt ccacggctga    35160
gtcccggcgg aagcgtaatc cgcatcggct tcatgcttgg tgaacagggt gtacgaatcg    35220
acggtacggt cggacgaacg cgccacgtat gcgctgactt tcgacgtgtt caggtcacgg    35280
ccgtcgcggg ataactggat gtacgggttt cgtacagcag cgtatcgagc ggcgtaatga    35340
tggacgacgt ctgcgtaact tggtgcggca gcagcgccac gttcgggcca ctcatgctat    35400
ctgcttcgcc gaaatcaccg ctaccatccg gctgcgcggc gaactgcatc agggacgaaa    35460
catacgggcc gtccatcggt ggcgttggcg ggttaggatc actggcggcg ttgtacggct    35520
gcgcggcgaa ctgcatcagg ctggcgtcat acacgaactg cggcggcttt ttataaacgc    35580
tgaccttcat ttcgtagtat tcccaacttt cgcggccact gcggacagac gtcaggcgga    35640
gcgtcgcgag caccgggtcg aacagactgg cttcgacatt catgtctgcc gctgcggttg    35700
catacggcca attccacgac gtgccgttga tgccggattc ggtgcgaact aacgtgcctt    35760
cctgattgta gacgcggatg gtgtacgtgg tacccggttc tggcccgatg tcgccgtcgg    35820
tgtgcggcac aggcttatcc gcttgcagga tacggtcgcg gtgcgcccaa gtcagggtgt    35880
acgtgtcagg cgtttcccg  gcgttggccg tgtaggtaag cgcggacggg acataccagc    35940
```

```
gttgcagcgt tgacgtcgaa gcgagatagt gctgcacgtt gcccggcggg tatgggcgga    36000
tctggcggaa gtccatgtcc agatgatcaa tcggcgcatc ttcaatcggg aagcggccac    36060
cgcccaatgt ccacggcagg atcttgatgt cgatggactc gttgcccgcg tatttctgcc    36120
agtcggtacc gccgtcgtac gtcgtcaccc aaagcatttc gcttttctgg tggcggaatg    36180
ggatggtatc gagtacgccg cgcgccacgg taatcacgtt gccattgatg gcgtcgatgc    36240
ggacaaactc ttcggcgatt tccatctgcg tgcgttggcc gtcaagaaca ggcttggcga    36300
tgcgcgccac gaagcccggc tgaacgtcgt cccacatgtc tgtcatttcg acaggatga    36360 tttgcgttga caggtagtca atgtcggcgg ccagcgatcc gaacgcaccg aagtcaccgt    36420
tgccacggat gtcgaagccg gattcacctt cggccatgat acccatgtca tacgcggcgg    36480
acatgtcagt cggcttctcg gcctgcgagt tgatgaacgc atcgttcggg ccgacggaat    36540
tcagttcacc gtccggtagc tgctgcacca gatccacgta cggcatttcg tacacgatac    36600
gtcgggcaat cgcgggcgtc aggtctggct catacccggc aggcggctcc acttggttga    36660
acgtgtttaa ctggaaggcg aactggtctt gcagcgcgac aatcttgatc ttgccgtccg    36720
gcagcgtgcc gtcttcaacg gtaccgacgc ggataacaac ttcggtcagg ccacgctgtt    36780
tcgggtcgcg cactttcagc acgtcgcccg gctgcacgtt ccatgcccgg cggtcacaga    36840
tcacggtgaa acggcggacg ttggttgacg cggcgcgcaa gtcacgctgt gccacctgca    36900
tcgccagttt cccggtaggg atgccgaggt attcaatcgt attgctgttc agacagccct    36960
gattctggat ctgcgcgagg ttgtggctac gcacctgctg gtcttcgtcc atgatcgggt    37020
tgtggtaggt cacgaccact tcgttaacca gattggcagg agacgcgttg gtcgcttcct    37080
gaatggacag cagcccggaa tccgtgtcga agatcggcag cgtgtcgaag tcgtagtcct    37140
tccggatcaa ccgcagggac agtttgcccg tcactttgct gacgtacatc gcaccgccaa    37200
tgtggtcgag gataagctgc atgaacgatt cgagcgtgtc ctgacggttc catcggatgc    37260
aaaggccgaa gttttcgtta aacagggtgt cggccacaag gcggaacgtc gtatcgtcga    37320
taagcgagcg tgacaggcca cggccccatt cgaagttcga ctggcactca tacaggatgt    37380
gcgcagggtt catggcatgg atttcgtgct gattgccctg cccgtcgtac cctgcatctt    37440
gaccagacat ttttccggat accagacgcc gccagtccac ccggccgtag agcggcgggc    37500
cttgaatttc cactgcttcg ggtatgggtt catggcgcag atcaggccgt cgaaatacgc    37560
ggtaacgaca ccacggaatt ccggctggcg gccaccgagc atgttcttta acttctggct    37620
gacggtctgc gtcggcgcgc ccatgtacag ttctagcggg ccatcaatgc cgccttccgc    37680
cttcgtgccg ccgaacaagt cttcgcggtt aatccggatg gttgtgttgc cagtgattga    37740
gcctgtccac gcggtacggt cgcccacgcg gatctcgaca atctcattca ccgggccacg    37800
gaaaaggccc ataaacaggc ccatgtagta tttgtaccca accgtaatct tcttggcttt    37860
acttcccatg tgcgtgcgcc tcgtcccatt cttgttggcc acggctgcgg ctttacgcag    37920
cagcgggttt gcggacttca tggcttccgc taccggtagc cttcccgtag gaattgttcg    37980
aaggtgattc cgaagcgctc ggccaagcgc tccgacccgt ttttgcaata cccgagtttc    38040
cggcatggcg cataaagatg cgcggctgat cctgcggctc gtcgtgtctg ctcattattt    38100
tttcgcctgt ttcgctttaa ctgctttggt tcggaagttg ccgaagccca atacctgcca    38160
gtcggctgtc cacacctcgc cgaataccac ggactgcggc gtgccttcct tcacctgcgg    38220
gatgtcgaag tcctgaattg ttgctggttt tgccgatgca ggcttcggcg cgagggccgc    38280
gttgatcagc accgaggcca ccagcatagc taacgcccac cacatagcga ttctccttaa    38340
```

```
aagattgggt tgccgtcgaa cggggaacgg tctggcagcg acgggatacc gccgaagttc    38400
gccagattgt tgaagatggt atcacaggcc gtactggtgc gcgggcatcc cgggtaagtc    38460
ttgaggatgt agccccggcc aagccgtcta cggtaccaaa gatggtaatg gtattcccgg    38520
tatgggtttc gatgccgcga cgttccacgc cgtacaccgg atctatccac tcgatgaagc    38580
cgcctgcgaa atacccatct ggccgtgtgg cgtatgcagc agccgtaacg gtacccgcgc    38640
caacggtaag gatcgtggca tccacgcgga aggcttcttt gttaacgcgg cattggccgt    38700
catacagcgc gtgcggacaa ccacggctcc acgacaggcg cagaccattt ctgtccatcg    38760
tggccgacag ggttgaacag gtgacagttg ctacggtagg gttttcgccc tgattgatgc    38820
tatcgacggt gccgacataa cagaccaccg ggtcgttatc gtcaaggtgc atccgtcgga    38880
tagtcagggt tacggggagc cgggggagtc ccgatgaaga ggccgacgac gggattcgag    38940
tttggcagcg tcagatttag cgcatccgtc ttagcctcgc ccgtttgttt aatcccgtcg    39000
tcggacactc ccatcggttc ccaaatgctc cccagcgcac ttactttagc gtctgcggag    39060
gtataacgcc agtatttatc cagcaggcga aactcgtaca taaatacggg cctgccgttg    39120
tcgttggacg tctcgataat gttgtaagac ataatgccct cttatgataa tggtaagggc    39180
gttgcaatcc tccgatcgtc gaaaaacttg aaggtcagag aaacttgact tacgcccgcc    39240
gagtcagtca accgttttat ttcgattccg tcaacatcta atcgcgctac ggggatatat    39300
ccgatgcgcc ggacgtcgtt tctggacgtc gccgggatgg actgtgacag gaatagccac    39360
tcttcatccc caacgatacg actcgaaatg atggtggtcg ggattctggt gccgtcgtac    39420
agttcgacca tgatgtcacg tttcgtttcc tgcgtcccgc cgatgtactg agtataaccg    39480
cagcgccgga ctacgagcgc gccgtcggcc ggttgatgtc gcgggacaga atgaagtcat    39540
tcgtatcgag cggcaggtgg aaagtcttgg tgcggccacg gagcgcgaac aggatctgcc    39600
ggaactgccg atccgctgtg cggccgttaa tggtgtacga cttcttcacg gtgccgtagt    39660
tctggccgcc cgggtcaacg atgaccaccg ggccggactg gttatcgaaa ttgtaggtca    39720
ggcggtcaga cgtgatttca ttggacgatc cccaatcttc cggcaggacg aagatgtgca    39780
gcccggtacg ggtgtagaca gggaagtctg accacgatgg cgtcaggtca tagttctcgg    39840
tgcagaagaa ccggacttgg gtctgtgaca cgctatcggt catctgctgg ccgttcatcg    39900
cctccggatc tgcgcaacgc gaaccggata caggcgcgtg cctcgcggcg tgtccgactg    39960
gaggccaaac gtcagcgtca tatgcccgcg tcaatgtcca gcccggcgat gatgttcgtc    40020
tcatagtccc acgtcgtgcc acggttgaac atgaccacgt cacccacgtt gaagtctttc    40080
acccggaact ggccgaagat gtccaccgac ccggctggcg catcgttttc cgtggctgtc    40140
atgtcgtgcc acaaaggcag gagtaacggc gactggccga cgcccgcgat ggtcgtgtcg    40200
agcagcgtac gcttttcctc ccacgcagga acgtcgcttc gaatgagcgg cgagggtgcg    40260
gatcgggcgt cgctgttctg cgccggactc ggaaatcatg acgtcagttt gccactcgat    40320
gcgctcggtg acgccgtctt tccagttcgg cagcggcagg aacaccgggt acgtcaggcg    40380
gacgtcgtca gagtaaggcg gcttcggccc aatgccttat ccggatcggc acgatgtccg    40440
cgataaagtc gttggcccgg ctaacctcga cggtctggcc gtcaaggatt agctggaatg    40500
ccatgtacgc cggggtgtcg gccgggacgt tggagtagat gcagtcaaag cggtacacgc    40560
cgtcggcgga gatcgtaaac tccccgctgt tcggattggt gccgatggcc gcagtcgcga    40620
cgacggcatg atcgatagac agggtgccgg agtcatcgac atacatgacc gccgtataag    40680
```

```
acccggcctt caacttcatc cacttcgcca tgtagtacgt ctggttggcc gccgcctgcc   40740
cgaagacgtc ctgaacataa agctggtacg ccccgttaag ggcgtcgtag attgcttggt   40800
taaactgttc gcgcgcgggc gcagtccgct caaagccatt gttattatcc cactaagttt   40860
ttcaacgtcg gtacgttgcg ttgaagaatc tgcattaccg ccttttctcc ttccggcgtg   40920
ttcatggctt ccggtacttt cgacctgtca tccaccagca cgaagcgaag accttgtggc   40980
gactgcgccg tctggccgcc gccgcgcgac tggttaagca cgttattcgg gtcatccttc   41040
gacagcacct gttcgccttt tgcagaatg gtcggaacct cgtcagaacg caagcccggc   41100
agtccgccat catggaagcg cgggcattcg cgaacatggc cgggctgatc ccgcccttca   41160
tctgcgtgcc gccagttgtc ttactgccga cggtgccgcc gttatgtttc gccacggtgc   41220
cgcctaatgc aacggccgcc gaaccgatgc cgccccccat agaggccaac gcgttgagcg   41280
ccatctgctg caagattgcc attgcgatct tctgcaagaa gtccgcgaag aaccgtgcca   41340
cggccacgcc gaggtttgag aacgcatcgc caatgctttg cgaccccggcc acgaccaacg   41400
ccatttcgtc aacgatggat gacagcgccg tgctcattcc gtccagcacg ccctgaacga   41460
cagtcgtgtc catcgtcgtg aaggtgcctg tgacgtccac cagcccggct ttgacggatg   41520
caatctgcgc catgatgcgg ctgaattctt ccggcgacat cgtgtctta atcttctgcg   41580
cgaaggcgtc aagctgctcg gccgacgacg cgatgcccgt attcatgttc tgatacaagg   41640
ctaccgtctg cgcgacggct tcattttcgg agataacccc ggcctgccgt ttggcattga   41700
tttcgtccag caggttttc ttcgtctcct gctgcgagtt taactgatcc tcaatgcgtt   41760
tcagttcttc gagtttggcc tgcgtggtcg cgtattccag attgcgtttg cgcaggtctt   41820
cgaactgccc ggccagattc tgcccgccag tcccgagttt cttcgacttg gcgatcagct   41880
gatcgtactg cgtattgacg gcggccagtt tagcggccag acgtcgtca aacgtggcat   41940
tcgggtcaat cttaacttcc ttcacaccga cggcggcatt caactcgttg tacttgttga   42000
tcagcgcctg taatgcgttt tcctgttct tgataccacc cgtcgtacgt tgctgcgagt   42060
tgaagagggt cgtttctgcc ttcttgcgcg cggccacaac ggcgtcaaga cgtttggtaa   42120
gggcgtcacc ctccgagccg ccaatcgact tagcgcggcg tactgcggcg caaattcctc   42180
gtcaatgatg gcgaggcggc cggacaggtt cttccgctgc tcggctttac gcgccgcgac   42240
gtccgctttt ttagccgcct cttccatctt gcctaactct ttcgtcaggc ccgcgatctc   42300
gcggctgcgc ttcgtgacgc ctgttcccgg gtcttgggtg aactggaagc cttcgccctt   42360
cgtgatagcg gccatgtcgg cggccagttg gttgacctgc ccgcgaatct tgtcagtcgc   42420
atcggcgttc ttcgcgacca tttcgtcgtt cagtttcacc cactgtttat tgacgttgtc   42480
ccaaatgcgg ccagtcgatt cgaggaagcc acgctgctct ttcgtcaggt cgtcgccaat   42540
ggacatggcc cactcggaca gcccttgacc aacgcccggg atcagtttca ggacatccgc   42600
gatccactta ataatcgcct gcgtggtgtc ggcgaacatc gtggtaatag ggcgcagcac   42660
cgataccgcc agatcgtaca gcagcgccgg gatggactcg acgacggctg ccagttgatt   42720
cccgaggttc ttgaagtccc ggatgatcgc gttgaccgcc tcgcggaagg tctgcgactg   42780
gtcgtacatg atggcaccga tgtcgtacgc cagcagcgcc cacccgacaa tcgggattaa   42840
ccgggtcagc cctttcaacg cgatgccgag aagccctacg gccccttgtg ccgcaatcat   42900
tctggccgcg acaccttcca gcatcgtgat aatgccatcg ccgattttac cgagcgtgct   42960
gaacagcgga agcaggtttt taaggcccga aatcatgccg ccgatgaact gcaccacttt   43020
cagcccggcc agaacgctta acgcggtgat cagcgtgtcc acgttctcga tgcaccacgt   43080
```

```
cacagcgtcg gccaacgtgc cgaacgcctc gccgagttta acggcggccg cccgaccatc    43140
ctcgctgttc aggaagtcgg tgatcttgtt aagcatctgc acgtacgctt cgataaagcc    43200
tgcgtcggcc aatgccagtt gaaacgcgtt catggcgttg cgggcgcgcg cttccatcgc    43260
atcgacacct ttctgcgccg tggcgagttg agcgtcaatc gctttggcct gctcgcgggc    43320
gaagttgata accgcctcgc cagtgacttc cccgttttcc atcgccttca tcagttcggc    43380
ggtggtcatg tccatgcctt tgcgaacag cgcgaaggcc gccggagacg ttcacccaat    43440
tggccgcgca gttcttccgc atacacctga cccttcgaca acatctgttc cagcgcgcgg    43500
aatacgcctt ccatgtcatc ttgtgacagg tggaatacac ggcccgcttt cgctacgctt    43560
tcgaagatga actttgagtc ctgcaatgac aggccgaccg ccttcgcgga tacggcgaat    43620
ttcgtgtacg actgtgacag ggtggtgatg tcgatcccga gcgtattcgc cagaccgacc    43680
atgtattccc actctttgtt gatggccgct tggctgttac ccaccacgtt cgcaattttg    43740
accatcgcct gctgacggtt cttgtacgcg tcgatcgcgc ctcccgccag attgatagcc    43800
ccctgaaaac cgatgtaagt ggtcgtcagc gccagcactt caccgcgaat acgttgcagg    43860
aaggacagcg tggtacggcc ctcgtctcgg aacagtgacc acgccttcga gccgtcgcgc    43920
gccgcttggc tgttccggtt cgtcgcggtg dacagcgtgt taagcgctgc ggccgattgt    43980
tggctggtgg agatcagccg ggcttccgca tcggacaggt tacgcgtgtc cacctgcgcc    44040
gctcgtaacg cggcttgggt agaccgggcg gccgtggccg tgtttcgcat ggccgtcgcg    44100
gctgcggaaa gccgttgttg gcggcctgca tctgaatacc taaagcgccc gtatcagttg    44160
tcgcggtgcg catctgctgt gctaacttga tgacgtcttg tcgcgcttgt tggtattcag    44220
tgcgggcgtt ccaagggtt gacacctgct ggcggtacag gtcgatttgc tgcgccagcg    44280
ccgagacggt tttattcgcc tcgttgagca ttcggacttt ctgtgcgacg ttttccactt    44340
ccttactgtt acgggccagt tcggtagtaa cgccgtgtac ctgattctca aggccggaca    44400
gggtgcggcg cgccgcttct gccgggctga cgatagtctg gatctgcgtg ccaagcggcc    44460
cgttgcccgg ttgcctgctg caccacgcgg ccgagggttt ggtacccgcg cgccgtcgcc    44520
atcgcctgat cagcctgctg ctgcaaccca cgaatgacct tcgcttgtgc ggccgcagcg    44580
gcagacgttg aaatgatttc gtcctgacgt tcgagaacac ggttgacctg cgcgacgctg    44640
gtgacgatac ccgcttgggc cgccccaact ttcgacgtct cgatcccgta tcgttcgagg    44700 tcgcggggttg cccggacacg cgctcggcct gattcgcttc cgcgcgggtt gcggcttcaa    44760
cctgacgtgt tacccggcca gcgcccgttc ctgtttctgc gtaaccttct cggtggaatc    44820
gtaggtcttc tggagatcgg cctgtttctg gcggagtcct tcggtcttgg ccgtcgcctc    44880
cgtcatggcc tgattctgcc gtttgaacac ctcgatcagc gagttgagtt taagcagttg    44940
gttcccggca ctttccagct ttttgtatgc ggcttccaga tcacgcgtcg agacttcacc    45000
gcgctcggct gctttacgct gttcgtcctg gccttcgcc atctgctcga tggcactggt    45060
cacagccttt aggggcttct ggctgtagtc cctcgcccgg attcgtagct cgacgtcttt    45120
actgttagcc atcagataat tccttgatta gttttttata ctctttcccg cctttcttgc    45180
cgttgagtac agcgccgata caggactgca tcagtaaact ttgggtgaca taacccgcgt    45240
ttacccggcg cttcgcgatt ttcgtttctg accacaaata tcctaacggg taatgccggg    45300
cggccgggtg tccctcggac atgaggaagg acaccgtggc acgaaggtta ttgtggaagt    45360
cgagaactat ttcgcgcttt gaccgggttt cgacccgcct cttcgccctt catcttgccg    45420
```

```
atctgctcca ttacctgagc gaacatcttt tttacttctt caacgtccga gaacgtcaga    45480
ccagcaatct ttttcaaggc gtcgaactgc accagaagcg gcagcgtctg taccttttcc    45540
agttcggctt cttcgtcggc ggccagcgcg atgacatgtg ccaccagccc cggcgcgtcc    45600
gataccagcg acacggcgaa gcgcccgta gcgatggccg tcaggtcttc cccggcagtc     45660
ttctgataca ggtcgaacag gccatcaagg tcgtgatagt ggacgcggat gattttggaa    45720
atgtcgtgga aggaaagccc acggacgtta aacgagccag ccttttttacc gtgtctggcc   45780 gggatggtga tttcttcgat ttctggtgcg taatctgcta atgacatttg acggatctcc    45840
tttgcgctaa tccgtcgtta atgtagcaca tacttgcaga taaaagaaaa gcgcccgaag    45900
gcgctttatc agtttggcat gtattacgag aaggtaatgg tgccagtcgt ggccgctttg    45960
ccgttcgcca gcgtggcggt gacagtcgcg gtaccagcgg cggcacggtt gacggtggtg    46020
gtcgccgtcc cggtagaccc ggtcgtcgcg ctgttaggcg taacggtcgc accggaaacg    46080
gtggtaaacg tcactgcatc gccctgaact gctgtgccag tgccgtcacg gacagtcacc    46140
gtacaaacga cacctgcgcc accggatgcg gccgaggtcg atgcaggcga aatctcgatg    46200
gtgcgttgcg tggtcgggtc aaccgctgcg gccgcttcga cgatgtcgat gtagacgcgc    46260
tgcgtgatgt tgttaagctg catggccttg aaggtgaagg acatgacctg ccagtcgtcg    46320
cctttcagtg cataatcgcc atccggcgcg atggacactt tcgggaagta gtagttcttg    46380
ttcagaccca ccgggttatc ggagatcatg cgcagcgcgc cgtacaccat gttggacttg    46440
ccaatgacca gcgtacgttt ctgcgcatca acgtcgtact gaaccgcgat ctgcacgttg    46500
cccgcgaggt cggctgaatc cggctcgatg tagatacggc ccgcttccag atcaatttcg    46560
tagttaccag ccgggttaac gacggtggca cccacgatag aagtgatgtc gcctgaacca    46620
acggaaatcg cgatggacgc gtccgccttg accatctgga agttagtcac gctgcgaaca    46680
cccgtcgggt tatcgtcagt ggtgccgagt tgatagtaac ggccgcgcat gatcgggttg    46740
aacacttctt tcgcgtcggt ctgctgcgtc tgagtggtgt tcgatacttc accgaggaac    46800
cacagcgcga ggttatccgc gttgatgttg tcacaggtaa aggtaccgcc ctgagacgct    46860
tccagcagga cggacgcatc catcacgcgc ataccgtgat cggaagagta gtgatccagc    46920
gtttcggaat cggtgttgat ggtgaattcc ggcgtgttac cgaaatacat ttcacccgtc    46980
ttacggttag tgccgtcttg gaatcggtca aagtagaccg ttccgcgacc taccacgtag    47040
ttgttttggt agttatcgtt cattctgttt ctcctgttaa ggattcctaa tgtccacttt    47100
gagtcctacc ctaacaggta ggaagaaaaa cgctgtatcg gacaagccgt cttcgggtgg    47160
cctgacaacg ggctgcgcga gtgtgagttt agcaatcttc ccacccaagc ggtagagggc    47220
cggatacatc ggttgtccgt tctcgtcctt cgccaccaac atcgccagtc gcttttccac    47280
ctcggccagc agttcgtacg ccgggtcggt cgggtttctc gggtcatctt tgacccaccc    47340
ctgcaccagc agcacccaat cgtccattcg tacggtctgt tcctcgttgg caaaggctcc    47400
gtagtccgtg gccttcgctt cgaggatcga cacgattggc agtttggacg tgaagtccgc    47460
gccgaatcgg tcgcgcccgc gatacacttt acctttcagg tcgtaggcgt atccgttctc    47520
aatggtgatc tgttcaaggt gcgctgtcaa tgctttaaga atgtcaagcc tttgactcat    47580
ttagacagcc tcgcaaagtt acgatggaat tcagcggcca ccatgtcgcc aatcttcggc    47640
gcgacggtgc cggacacttc cgcaaagacc tgatccacgg acggcccgta cagcaatgcc    47700
acccggcccg gtacgagcca tgatttgtgc tgcgagcgtt tattggacag ggattcccgg    47760
cagaaagtcg cacggccaga ccgacgttat actggtcttc ggtgaggctc gcgcctttgt    47820
```

```
ttagccgcac aagaaacgca tttttcaggt acgtcgtctt gcccttcttc acccgcacct   47880
gtacaccgcc gggccgtttg ctattcgtca ccattgcgcc gcctgtaacg aaacgggcga   47940
ggctggtggc gcgcttacgg ccgacaatga cagcttcgag gttggatgtg gtggcgcgct   48000
tagtcagctt gaggcggtct gcgttgagat acccggttgg gaaggcaatc tcgtcggtca   48060
tcgacttctt gataagggtc atgcccttgc cagcagccac gctattaatc gccatgcgga   48120
tcgaattgtt agcgatttcc ggtacctgtt ccagataccc tttcaactcg tcggagccga   48180
tcgctaacac gttaacaggc atcagtcggc cctcgccacc tgccagacga tttccactgg   48240
cccgacgata ggttcctgcg ttttgagtac caaacgggcg ttctcgtacc ctcggccgtc   48300
atgatgatgc tatcgccttc ggacagcatg accccttttg catttaactc gtcacgcata   48360
aaaatgatgc gctcgatgcc ctcgataacg ttagcgtaac caccgttttc caagtcgcca   48420
tgatggcgat cttgttgtgc cagcggacgc taatgtcgtc tacgatgaca tcctgcgcat   48480
aattctcata gcgagcagcg acagacaggg acgcatgtac gtccctgcga gccttcgctt   48540
taattgcggc gaagttagaa gccatgatta gacttcatct tccgcgccag acttttatc   48600 gtctttggcg tttttcttag caccgtcagc cttcgtcttt tttggacgcg tcagctttcg   48660
cctgctgcgc tgcggcttcc tgtgcagcct gattttcaac gtcaacttcc atcaccgggc   48720
ggccgatggc atccgggttg atttgttga tgctgtccag ttcggcttgt ttgaaatcga   48780
agatctcgcc gatggacggt ttgatacgcg cgccgtcgcg gtaaacgatg acggtctgga   48840
gaactttacg ttttgcatg gctctttcct caaagcgacc cgcccggtac aggcggatcg   48900
taggtttgaa ttacgggtta ttaggacatc acggtcagca ggaacgacgc gttcgggtcg   48960
gccggaacca tcagtggtgc gccctgagac atcaggtatt ccacactcgg gtcttcctga   49020
tcccacattt tcgggaagta atcaagcgcc tgatagcccg cacctttgtc cagaatcgcg   49080
ccgaagcaac gtacgccctc gatcgccgag gaaatacccca ttaccgcctt ctgcttcatc   49140
aggaactgtt cttggtcgtt ctggtcgcgg tatttctgag tgttcaccca aatacgcata   49200
cggccagcac cgttagcccc taccagttcg cccatgtact gaacgccttc cacgtcgtcc   49260
cacaggcggg taacgttggt ttcagaccca cggatggttg agtccatcag gccgtctttg   49320
ccccacagtt cttaccgcc gaccttgacg aactgatccc aagcgtcgcc gccgaagacg   49380
tagtcgcgga tcacggtgcc ggacatggac ttatcggaca ccagacgttg accgtcacgc   49440
aggtcagcaa tcatgtccat cagggtgacg ccgctggcag tccagtcggt tgtcatggtc   49500
agcgctgcat cacggccgaa gtctacacgc accagcgggt agtcctgacc ctgaacgtca   49560
acgtaaccgt attgcgcagc ctgcgccgcc atccattccc acgtatttc gtgcatggcg   49620 cggtgtttca tcagcagata tgcgatgaca cggtcgcggc gctgcgcgat agacaggtg   49680 ccagtaccca acgcttcacc cggctgacgc gggatgatca tgttagggtc gatgacatgt   49740
ttcggcttca cgtaggcagg tttaaaagtc ttcgtgttgt agccgctttc tttgatcacg   49800
cggccctgta cgttgggtgc aacgaacgga gcgacgcggg ttacgtcctg aataacttta   49860
tcgaaggcaa tcatgtcttc ctgaaagtta atctggcgcg ggaaccattg caggaagaac   49920
gcaggcagcg ttttcagctt gcgctgtact tcgagcagtt ggtaagtagt gtaaagtcca   49980
gccatttgcg ctgctcctta gtacagattg ccgatgtgga tgttagtacg gtcgaagacc   50040
gcctgacgtt ttgccagcgt atcaagcgac gcgtgccaac cgagggcagc gtggttgaat   50100
acaccaccga tgtagtacgg cacgttctgg ccggacttcg cgggctgcgc tgcgataccg   50160
```

```
atagccacag actgcggtgc tggtacttcg tccggagacg tgccagtggt cgcagtcggg   50220
tcatgtggca ccatagcgcc agcggcgttc ttcgcgataa cctgatagat ctcgatgtca   50280
gcgccagcgg caccgccttc ggtcacaata tccgcttcac ctgcgaagat ttgggttggc   50340
tcccaagagc cgaggtcgcc gtttccagcc agatagttag gcaggctgga ggcggccatc   50400
atagtcaaaa gattcatccg aagatcccct attacttagc catgttgttg ccagcgacag   50460
cggtcattgc cgccatcagg ccagccgttt ctttcgcgcc ttcctgctcg ttgcctgcat   50520
cggcaccagc gttaggatgt tccgcgcttg ccatcactga atcgaacggg ctgtcaccct   50580
tcgcttcggt tccggtttta cccggcgcag cagcgtcaac gacggtagtc gtaacagcgg   50640
ctttcggttc ttcggcggaa ttggtcagca ttgcagtcgc gtcttcaacg acatattcg    50700 tgttgaaggc gatgtggttt gccagtttgg tacggttagc cgctgcatca cagcccatga   50760
tcccggcaat gcgggttcgt tcgttggtcg ccgcctctgc gcgggctgcg tccatttctt   50820
cttgcgtaaa gctcattgcg ttcgctcctg agtgatccgg gctgttatcg gacggcccgt   50880
tgaggaattc ggtaacagcc ttcgaaggcg ttgataccgc gtcaattaga ccgattgaca   50940
tcgcttcacc agcgttatag cacatcgctt cggtgtcgcg caccactttc ggatctaaat   51000
ccctgttttg agcgacaaga ttgacgaagt cggtacgcat tgaatctacg ctcgcttgcc   51060
agtctgctcg tacttcatcg ctcattggtt cgtacgggtt gccgtcggct ttgtgctccc   51120
cggacttgat gatattcacg gtgataccga tgtccgccaa catcttcgac atgtcgatgt   51180
ggagggcgat aacaccgatg cttccggcac cgccggacgg cgttacaacg attttatccg   51240
ctgcgctcgc caacgcatat gccgcagaat agcagtttga atcgacaacc gccagcgaag   51300
gtttctcgcc gcgtgtatca aacatttcct gtgacagctc gaaacagcct gctgcttccc   51360
cgccgttcga gttaacgtcg tagatgatag cctcgacatc cgggtcggcc agcgctgcat   51420
tacgctgact gcggataaaa ttgtagcccg tcacgtagcc gtagtaatac cgccatagc    51480 ggttaatcag ggtgccgtga atcgggatga tggcgaggcc gttcgagaag cgaaaggct    51540 tgtccgcaga cggtcggcca acgccgtacg ctgcacacag gttttcgcgc atctgctgtt   51600
cagcgcgctc ctgaaaatct tcgtcatcgc aggacatcat ctgctgcatg ttggtcagca   51660
gcgtcgggtc attctcgcga atggcgatcg gctggccgtt cattcgactg agcgccattg   51720
agacgctcgc tcttacgtgg ttgctcattc cttcgtatcc tcttcgttgt tgtccgagcc   51780
agtgctgcca gttgaaccgc ttgcctccgt cccttcgacc atcttgccgg agaaatcaag   51840
gcccaaatct ttgatgatgc cttcttcgcg ggcgcgctgt ttgaatactt cgcggaagtc   51900
cccaccgagg cgggcgattt ctgcttcgta cgttgacagg ccattcttga tgcgaaggat   51960
agcggcttcg gtttctttct tctcgtcgat ctggccgcga ctcgcgccga tccattctgc   52020
gttgcaaagc gcgtcacgtt tcatcgggtc gtagaagtcg cgccaagtga agcccggcgg   52080
cagtggaaca ttaccagcgt taacctcttc ttccaaccac aacgtataaa tcatcgacgc   52140
gaaacggtcg gctaccagct ttttacggct ttccatgtac ttccacgttt cagccatcga   52200
agcgcgggca gaagagtagt tcgttttcgt atagtcgcgg ctgaactgct cgtacgaaag   52260
gccgagtgat gcggcgatgt tcctgagcaa cgattcttca taatcggttc cgactccgcc   52320
cggcgttcct gcgggctgca ttttcagttt cgtaccgggg aacaggtgcg ggattttcgc   52380
cccgtcgatt gcgatgtttt tcgatccggc gatgtactcg gccagactcc ccatgtaggt   52440
tttcaggatg tcgccgaacg gcgtctgtcc catcccatc tgattgaaga ccacgtcaga   52500
cggcaattct gattcgatgg cggccgcgta ggtcgcgttg acgatggcgt tttgcagcgt   52560
```

```
gacttcctga aagtttcggg tcatcttcat ctgcttcaac gctgcgacca tttcactgat    52620
accgcgagtc tggcccggca gcagcgcttc gatgatgtgg atcatccgac gtcggcccca    52680
atcgaagcga gcgggctggt attcccatcg ccattgttcg aggtcagtcg ggtcgcccgg    52740
gaacgcttta cgcagccagt agccgatcgg agcgcccatt tcatccagtt tgacgccgga    52800
gcgcagatac ttgtcgtcca tgatgttgtc cgggttggac agacggtacg gcgaaatcat    52860
ctggatcgca gtgccgaacg gacggcgctg catacgggtt ccctttcggct tcatccactc    52920 gcatgacgcc agaacttccc cggtcatgat gaagccgcca acggccagac ggacaagccc    52980
ggtcagcgtg ttcatccggc gggcatcgaa ccagttttca ggagactcgg ccaccatgtt    53040
gaagcgcgcc tcgactactt cctgaaattc atccgcccaa ccttccggcg cgccgagcac    53100
cagcgaattg ggtttcgagt tgagtttgta ctgcgagccg acgacgctgt cacggtgaat    53160
cgccaccgcg ccaaatgcgt agccgtcgtt ctgtacgatg tcctgcgcac gcgaaagcgc    53220
cagcgtaccg tcttgggcga tctgctggtc tggtgaaatg atggcaggcg tccagcggaa    53280
catttcacgc gtgttccgtt cagccccctc taagccgcca ccgagtgccg aaggattctg    53340
cggcgtggcg tccaacgtag cgacgtcggc ggtctttgcc gctttcttcg cccgttgtgt    53400
agtgcttctc tttttctcgg tcatgggaat aagaatcctg ctggtgaact tggtaggccc    53460
atgaaggccg cgcaagggtt gtccgaatta atcgcgtttt gcagtcgaac gatgtaggcc    53520
cataggcttt gtcggttcgc tgcggtatat tccacgcgtt cactgttctg atccaccacg    53580
acgcgcaccg agccgccgag gtttaattgg tggtacgcat ccatcgcttc tttgagcatg    53640
aggcgatatt gcgcgcggca ttcttctggt gtcatggtgg ttctcctatg ctaacgccat    53700
tgcgagtttc tcgaaactgt attcggtatc tttcggtgca tcaataggtt catcgctctg    53760
cggtaaaata accatgctgt tatcgtccca ctcggccgcc catgatggcg ggttatccca    53820
atctatctgc tcaatcccga gcacgcggcc actgacgcaa attcccaata aataatatgc    53880
caagtcccac gtttcgtttc gggcgtggga tgggttgtgc cagcctttct cgtcacgcgt    53940
ctccgtacac agttcggcga ataccgcgtc gcccatccag tccgggatgt ggtacatgcc    54000
tttgcccggc tccacgacgt ccagtcggcc gttcaggctg tctttcatca cgttcgagtt    54060
aatcatcagc accggaacgt cgccgcgtgc gatggctttc ttgtctttct ggttggagtc    54120
cggtagcgct acacgggtgc gcgggttgtt cgctttcggg tcgcccttca ccagacagaa    54180
gcgcccggtt ttcccttcct tccgcagttt ccggaagaat tcgtacgcgt tgcccgttac    54240
cccggcttca ccaccggagt cgcacgcggt catcttgatc ggcagcgaac ggcccgaatt    54300
atcggacagc ggatacgtct tgttcatcac ttcggtttca atgagatccc aatcttcgag    54360
gtacgcgccc gggtgcagga ttttcgggtc gccatcgtca tcgagtcggc gcgatttcgt    54420
gatgttgaag cggtcgatca gataggtgtc gaacgggtag ccggggccac accatgcacc    54480
gacacttcaa agctatgctt ctgcacgtcc accgtggccg ccaagaaccg cacattcttc    54540
ggcaccgtct gttccggcca cttctcggcg cgggctttca gcgcttccgg aacgcgtacc    54600
gtctcgatcg ccttcggcac gtacggttcg cccatgtcgt tgttccagaa tttcttcaag    54660
gactcttcgg acatcgtacg ctcgtagtca tccatcgcat cgaggtagtt cagaaccagt    54720
ttctgccatg tgatgaatgc ggccgccgtt ccgcgaagcc agaaggacgc gaacgacgag    54780
cgcatcggta ccccgccag ttggcccaac tcgttgacat gacagccttc cggcacccac    54840
atcccccaca ggttcatttc atacttatca accgggtcta tttcgcagcc gcagtgtgga    54900
```

```
caggccatgc gcactgtctc cgacttttcg aggttggtta gagggttgcc atcggcgtct    54960
ttcgtgttcc acttcaaaag ctggaaggta ccttcgaaat actggtcgca atgcggacac    55020
ggccatttcc agcggcggcg gtcgccacgg ttgtacaggc cgacaatccc gtcacacggc    55080
ggggcttcgt ggggcgtgcg cttaatccag cttgggtctt taatcgggcg cgatggcgat    55140
gactcggctg cacacatggc aaacgacccg aaggtcgtcg tacgttttga tgcgaggtcg    55200
aaggcgttac cgtcgccgcc gatgtcgtcg tcaatacggt cgtagtcggt gatgatgatg    55260
cgaccaacgg gacgcccggc cagttcggtt actgacggat aactcaacgt caggatgatg    55320
cctgtgacgt agtgtttgtc gaatttgttg tcggcgtcgc ggttcttcat cagcatttcg    55380
cccaccttcg ggctatggcg gtgaagacgg tctacacgtc gcatcgagaa gtcgcgcgcg    55440
gccgttgacg tcgggcagta gaccatcaga tccatcgggt caactttcac cgaatagaca    55500
atgctattca ggatcagcgc atcggtttta ccggactgcg ccgggccgac aaaggccatc    55560
ttgtcgtacg cccggctgtt catcatgttc atcggctcga ccatgtacgg cgtcgtcgag    55620
ttaagccaat ccccgacgta tgcgccgggt tggttgacgt agcgatactt ggcggccgcg    55680
tcggccaccg tcatgcgcat tggcggccgt aactgctcgg ccaccgaact gataatctgc    55740
ccgatgctct taaacttcat cgtcgccac ctcgtcgccg ttgaacttat cgatcagcgc    55800
gctcgacagg tcgttcagca tggcgtcaat ggatgacgtg atgacctgac gttgcggctc    55860
gctgagtccg gcctgacgcg ccagcgtgtc gggaatgagc aacatcgaca tgcggagcac    55920
cttcaccgcc tcgccgaagt gctcgatcac cttctcggtt tcccacaggt tgcccgcttt    55980
gatgtcgaag tcctgctttg cgcgctgccc ggcccaaaac tctttcgaca actccttcgg    56040
cagatccttg aaattcatgc ggcgcaggta cgtctcgaca tcgtacagcg gcttaacgag    56100
gtacggggcc acttcgtgaa ccgcgtagat cgggtacccg ccacgctcgc cgacaggcgg    56160
gacatccatg attttcggcg tgatgtcccg gcgctccatg cgaaacagct tcgccagttg    56220
cgtgatgttg cagccctgaa agatcatcgc ttcggtatcg gcgtccggcg cattagagcg    56280
gcgattccgg gttgccagtg gcgcattact cttcgtcatc ccataccct ttattttcg    56340 atttcttgcg gcgtttgatg cgccctttga tacgttcgag cagttcgaag aacgcgtcct    56400
gcacgtcttc cttttcgacc agcgcctgta tgactacgtc gtccgccgtc tcggccagaa    56460
gcccgttcgg tgttcgcagc atggctttga actggtagat cgtaaccggg tacttctgcc    56520
ctgacggtgc aatcggccat tgaattgcag gaagcgttcg agtgaccacg gattgtcgat    56580
gtagacgatg acgtggccgc catgctggag gtttaaaccg tgtcccgctg actgagggtg    56640
cgcggccagc agtcgaatct ttccggcgtt ccacttcttg atgcacttac cgtcatcatc    56700
catgaccacc agatctttaa accgctcttt cagtcgttcg agggtcggct tgaagtgata    56760
ggcgatcagc acgttttttat cggccagcgt ggtttccagc agttcttcca gtgcatcgaa    56820
tttcaggtcg tgcagcctgt acgtgtcctt ctgcttaatg accttgtcgt cttgcgttat    56880
gccaacgatt ttcgtgtcgt agatgaagcc tgagcacatc tgcaataact cgactgcaa    56940 agacgcggcc tgctccgctt cgatcacgat tgggtcatcc agatgttcat cgaaatcgtc    57000
cggcataatc tcgacgaggc tctcttcctc catcatgcgg taccgctccg ccgtctcccg    57060
tctaactcga ccgggacagg aacgaaattc ggttcgtgca tgtcaaggta gtcttccgct    57120
ttcatgacta acatatatc agaaatcttc cgaataatct cgtctccgc accgggcgaa    57180 gtttccattt gaagttgtag cggttctgcg tgaagtagtt ttcctgataa ccgccgatgg    57240
tggagccaaa gcgctcgcct tcgtccagca ggtaaatttg cgagaagata cccatgtacc    57300
```

-continued

```
cttcggccgc aggcgtggcc gtcaactcga cgatccgttt gatgtacttc cgcacccggc  57360
gcagcagttt gaagcgctgc gaggtgtggg atttgaacat gctcgactcg tccagcacca  57420
cggcgtcgaa cggccatttc gtcttgaagt gctcacatag ccacgcgatg ttatccacgc  57480
tgatcgtgta gaagtgacag tccttactcg cggccgctgc gcgctctttg gcgtttccgg  57540
cgataatcga catcttgtag aagcacagat gcccccactc gtcgaattcc gtcggccacc  57600
cggtacgggc cactcgcttc ggcgcgacga cgaggacttt gttgatttcg ccgtccgcga  57660
tcaggtctag catggccgtc ccggtcatga cagtcttacc caagccgagg tctacgaaca  57720
tgccgcagta cggatggtct ttgatgaact ggacgccttc gtcctgatag tcgtgcatgt  57780
cgctgcggtt cagtttaacc gtccgcaggc agtacgcgag cgctctactc aaaggcgata  57840
atgtagtttt taaagtctgc aaaattgtcc acccatgtca cgttagcccc gccttacgca  57900
tttccttgtg gcggtgatac tgctgcgccg ttggttcttc gccggggcgt ttgaattcga  57960
taaaaagcac aatgccgcca cggatcagca cgcgatccgg gacggctttt ttgccgggga  58020
ggtgaatttt gacaccccac cccgcgcccc tgcgcgtatt cgcagcagcg cttttcgacc  58080
ttcgattctc tgattatcgg ctcggccatg ttaatcctta cggtagaaat aaccttccca  58140
cccggcagcg ccaagcggta gcccttcggc cacggtagtt cggccgccat gcaggaataa  58200
ggtcgtccac ggtcagcggg ctgtcttccg gcacttcggt tacgatttca tcgtggatgt  58260
gcatgacgat ccggaagccc atgcggtgcg ccttttcag accttcggcg agcacgtcgc  58320
gcgccagcgc ctgaacgatg ttttccacca gcttaccgcc gtggctgtaa atcttgcccc  58380
ttggtgccgc tgccttccac cttgccttcg tactggaagt tggtctttgt gtacttctca  58440
ccttcttcgg cccttttctga acggtcatct ggcgctcgac cagacgcgga cggaagtaat  58500
acattttgcg gccagacggc agacggatgg tcaggaaagg ttttgtgtat tcgatgatca  58560
gacagcccca tacgacggcc tgacgggtac ggataacctt gaataccgcg ttttcgaggt  58620
cataccatgc gcgcacaatt tccgggcaaa ggtcgcggaa cgcctgtacc gactcttctg  58680
cctcttcctg cgtcatgtgt acgcccatgt tttcggcgta gccccacagt ccggtcttct  58740
tgccattctc gtccatgtgg ccgccgccga ggcgatagcc cgcgccgagg gtagcaggtt  58800
tggctttcgg cggtgtggct tcgtttcttc gtacggcagg tgcagccagt gagccgcgaa  58860
tgaacggtaa aggtcgtgct tggccgccag cgtgtccatg aaatttgtca gccacccgat  58920
aaccacggat tcgatggacg acaggtcggc aacgatgaac ttgtggcccg gcgtcggatg  58980
aaggcggagc gaatgcagcc caccagcgcg tccatcggct cgcccacata cagcgtcaac  59040
gca                                                              59043
```